(12) United States Patent
Hoeppner et al.

(10) Patent No.: US 11,149,319 B2
(45) Date of Patent: Oct. 19, 2021

(54) SYSTEMS AND METHODS FOR DETECTING CELLS USING ENGINEERED TRANSDUCTION PARTICLES

(71) Applicant: Roche Molecular Systems, Inc., Pleasanton, CA (US)

(72) Inventors: Corey Hoeppner, Dublin, CA (US); Ronald T Kurnik, Foster City, CA (US); Xianxian Liu, Sunnyvale, CA (US); Soni Shukla, Saratoga, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 759 days.

(21) Appl. No.: 15/846,730

(22) Filed: Dec. 19, 2017

(65) Prior Publication Data

US 2018/0179600 A1 Jun. 28, 2018

Related U.S. Application Data

(60) Provisional application No. 62/436,722, filed on Dec. 20, 2016.

(51) Int. Cl.

| | | |
|---|---|---|
| *G01N 31/00* | (2006.01) |
| *C12Q 1/6897* | (2018.01) |
| *C12Q 1/18* | (2006.01) |
| *C12Q 1/02* | (2006.01) |
| *G01R 1/04* | (2006.01) |
| *G01R 1/20* | (2006.01) |
| *G01R 31/26* | (2020.01) |
| *C12Q 1/10* | (2006.01) |

(52) U.S. Cl.
CPC .............. *C12Q 1/6897* (2013.01); *C12Q 1/02* (2013.01); *C12Q 1/10* (2013.01); *C12Q 1/18* (2013.01); *G01R 1/0408* (2013.01); *G01R 1/203* (2013.01); *G01R 31/2601* (2013.01); *G01N 2333/24* (2013.01)

(58) Field of Classification Search
None
See application file for complete search history.

(56) References Cited

U.S. PATENT DOCUMENTS

| | | | |
|---|---|---|---|
| 8,829,473 | B1 | 9/2014 | Griswold et al. |
| 9,133,497 | B2 | 9/2015 | Frei et al. |
| 9,481,903 | B2 | 11/2016 | Rey et al. |
| 9,540,675 | B2 | 1/2017 | DeForest et al. |
| 9,546,391 | B2 | 1/2017 | Rey et al. |
| 2009/0287417 | A1* | 11/2009 | Palo .................... G01N 33/6872 702/19 |
| 2014/0272928 | A1* | 9/2014 | Rey ...................... G01N 21/763 435/5 |
| 2014/0272939 | A1* | 9/2014 | Aghvanyan .......... C12Q 1/6804 435/5 |
| 2015/0218613 | A1 | 8/2015 | DeForest et al. |

FOREIGN PATENT DOCUMENTS

| | | |
|---|---|---|
| WO | WO2014160418 | 10/2014 |
| WO | WO2014164768 | 10/2014 |
| WO | WO2015164746 | 10/2015 |
| WO | WO2015192043 | 12/2015 |

OTHER PUBLICATIONS

Fekedulegn, Desta B., et al. "Area under the curve and other summary indicators of repeated waking cortisol measurements." Psychosomatic medicine 69.7 (2007): 651-659.*
Mar. 8, 2018 International Search Report & Written Opinion for PCT/EP2017/083735.
Bernard et al., "Microbial community dynamics based on 16S rRNA gene profiles in a Pacific Northwest estuary and its tributaries," FEMS Microbiology Ecology, vol. 52, No. 1, 2005: 114-128.

* cited by examiner

*Primary Examiner* — Anna Skibinsky
(74) *Attorney, Agent, or Firm* — Pamela C. Ancona

(57) ABSTRACT

Accurate measurements of the presence or absence of a target cell in a sample are provided. For example, the sample can be mixed with a plurality of transduction particles capable of binding to the target cells, the transduction particles being engineered to include a nucleic acid molecule formulated to cause the target cells to produce a plurality of detectable reporter molecules once the particles bind to and deliver the nucleic acid molecules into the one or more target cells. A set of signal data points are received that are associated with a quantity of reporter molecules and the signal data points are analyzed to accurately detect target cells in the sample. Systems and methods are disclosed.

9 Claims, 16 Drawing Sheets

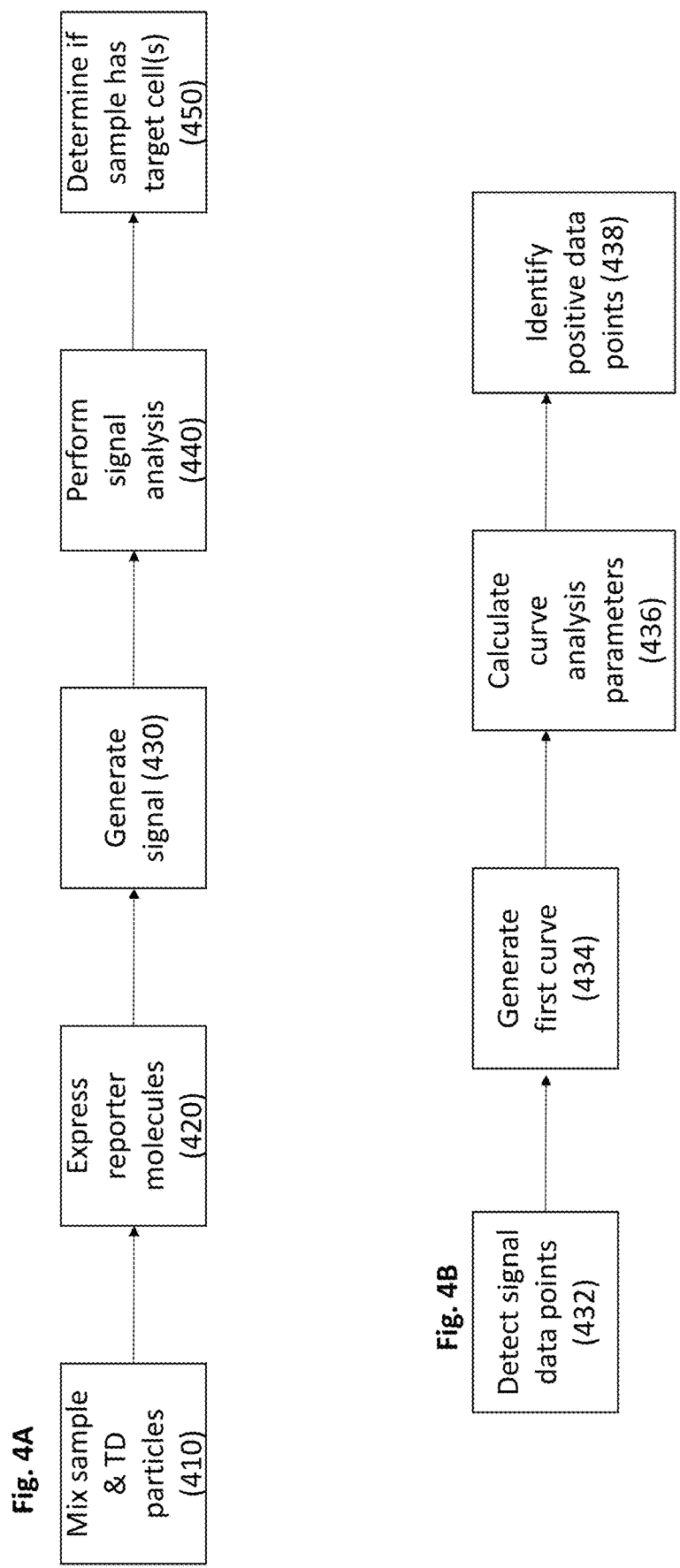

SYSTEMS AND METHODS FOR DETECTING CELLS USING ENGINEERED TRANSDUCTION PARTICLES

CROSS-REFERENCE TO RELATED APPLICATIONS

This application claims the benefit of priority of U.S. Application Ser. No. 62/436,722, filed Dec. 20, 2016. Reference is also made to the following U.S. patent applications: Ser. No. 13/802,461, filed Mar. 13, 2013; Ser. No. 14/048,974; filed Oct. 8, 2013; Ser. No. 14/480,269, filed Sep. 8, 2014; Ser. No. 14/611,902, filed Feb. 2, 2015; Ser. No. 14/617,631, filed Feb. 9, 2015; and, filed Dec. 15, 2015. The disclosures of each of these applications are incorporated herein by reference in their entireties.

FIELD OF THE INVENTION

The embodiments described herein relate to systems and methods for detection of cells using engineered transduction particles.

BACKGROUND

Detection of bacteria, especially drug resistant strains, is a critical step in diagnosing and limiting spread of bacterial infections. For example, methicillin-resistant or methicillin-susceptible *Staphylococcus aureus* (MRSA and MSSA, respectively) are drug-resistant versions of the common *Staphylococcus aureus* bacteria that is carried by a significant portion of the population in the U.S. Most infections of MRSA occur in hospitals, and can have a high mortality rate (MRSA infections kill approximately 19,000 people in the U.S. every year). In addition, carbapenem-resistant Enterobacteriaceae (CRE) or carbapenemase-producing Enterobacteriaceae (CPE) are Gram-negative bacteria that are resistant to the carbapenem class of antibiotics, considered the drugs of last resort for such infections. Like MRSA, hospitals are primary transmission sites for CRE- and CPE-based infections Accordingly, there is a need for efficient, accurate and rapid identification of the bacterial strains (including their phenotype and/or genotype and other molecular targets) that cause infection, such as MRSA, MSSA, CRE, and CPE. Particularly important is the ability to identify the bacterial phenotype and/or genotype and other molecular targets from a variety of different samples (e.g., human samples, environmental samples, plant samples, veterinary samples, food samples or the like), so that the appropriate treatment and control regimen can be started in a timely fashion.

One known method for identifying bacteria includes bacterial culture. Culturing is highly sensitive, but often takes two to three days (or even longer) to yield a result, and is therefore not suitable for rapid diagnosis or for efficient screening purposes. Known culturing methods are often performed using systems that require highly trained personnel to perform the assay, and are therefore not suitable for use in a variety of different settings. Known culturing methods are also prone to contamination, which can result in false positives and/or misidentification of the bacteria. Moreover, known culturing methods employ specifically tailored culture protocols for identification of various bacterial species, thus testing a broad bacteria panel can rapidly elevate the cost.

Other known methods for detection of bacterial cells include isolation and analysis of nucleic acid such as DNA or RNA. Known methods for isolating nucleic acids from a sample often include several stringent sample preparation steps that require expensive and specialized equipment. In particular, such steps include 1) removing the proteins within a sample containing bacteria or cells by adding a protease; 2) breaking down the remaining bulk sample to expose the nucleic acids contained therein (also referred to as cell lysing); 3) precipitating the nucleic acid from the sample; 4) washing and/or otherwise preparing the nucleic acid for further analysis; 5) analyzing the nucleic acid to identify the species. After preparing the sample, known analysis methods can include polymerase chain reaction (PCR), gene sequencing, gene fingerprinting, fluorescence, immunoassay, electrochemical immunoassay, microarrays, any other suitable technique or a combination thereof. PCR has found widespread commercial usage but often requires multiple steps involving expensive reagents and instrumentation. Many known methods involving PCR are not suitable for bench top testing (e.g., they require relatively skilled personnel). Moreover, known PCR methods employ thermal cycling and/or elevated temperatures, which can increase the cost, time and/or complexity of the analysis. Finally, because PCR methods for detecting DNA sequences lyse the sample cells, such methods cannot distinguish between live and dead cells.

Some known systems and methods for cell identification include the use of bacteriophages to identify and/or detect certain bacteria. In some known methods, phages that are tagged with a reporter molecule can be used to target and infect a specific bacterial strain. After infection, the phages can undergo a lytic cycle (i.e., break the cell wall killing the target bacteria) and/or a lysogenic cycle (i.e., replication of the phage along with the bacteria without killing the bacteria), followed by detection of the amplified progeny phage. Such known methods relying on phage detection often include limiting or complex steps. For example, some known phage detection-based methods for identification rely on phage replication (during which the bacteria can be lysed), and typically require cell culturing for facilitating this process. Some known phage detection-based methods require removal or "unbinding" of specifically bound phages from the samples using carefully metered and/or pH controlled reagents.

Moreover, some known phage detection-based methods rely on careful metering of the amount of phage added and/or include opening or closing of the reaction chamber to add/remove reagents, which can lead to contamination and/or premature mixing of reagents leading to erroneous results and making the assay complex in nature.

Other phage-based methods employ bacteriophages that are engineered to deliver into the target bacteria a nucleotide that can include a reporter gene, which cause the target bacteria to express a reporter molecule. Some known methods include phages that replicate during the assay, however, which can result in an undesirable lysing of the cells within which the reporter molecules are to be produced. Other known phage-based methods employ bacteriophages in which the replicative functions are suppressed during the assay conditions. Such known methods, however, are difficult to implement due to the tight range of conditions (e.g., temperature conditions) under which the replicative functions will remain suppressed. Such methods are not easily controlled, and thus can result in lytic activity. Still other methods suggest the use of temperate phages that undergo a lysogenic cycle instead of a lytic cycle. Such known methods, however, are also susceptible to sporadic lytic activity. Incorporation of native phage life cycles may also lead to limiting of the reporter phage host range due to superinfection immunity by target cells that may be lysogenized with a prophage. Thus, although known methods of this type have been performed in an academic setting, they are not applicable in a clinical setting.

In addition to the above-described drawbacks regarding the use of phage-based methods, known methods do not employ automation or instrumentation that enable a "walk away" bacteriophage identification system. For example, many known systems do not accommodate closed system handling and/or measurement of a signal that is produced by certain reporter molecules, such as for example, a flash luminescence reaction. Thus, known systems and methods require skilled personnel and intimate handling of the samples, which can increase the possibility of false positives or negatives.

Thus, a need exists for improved apparatus and methods for rapid, cost effective and facile detection and identification of bacterial species in clinical samples.

BRIEF SUMMARY

Embodiments can provide accurate measurements of the presence or absence of a target cell in a sample. In a specific embodiment, the target cell is a pathogen and the methods and systems described herein can be used to identify whether the target cells in the sample are resistant to an antibiotic or class of antibiotics. In a specific embodiment, the sample is mixed with a plurality of transduction particles capable of binding to one or more target cells. The transduction particles are engineered to include a nucleic acid molecule formulated to cause the target cells to produce detectable reporter molecules. The sample is mixed with the particles under conditions sufficient to insure that the particles express, bind to, and deliver the nucleic acid molecules into the target cells and thereby express the reporter molecules. A set of signal data points are received that are indicative of the quantity of reporter molecules and a curve is generated using the signal data points. The curve is then is analyzed to provide an accurate measurement of the detectable signal and in so doing, the presence or absence of the target cells in the sample can be measured.

Thus, in one aspect a method of detecting one or more target cells present in a sample is provided, the method comprising the steps of: (a) mixing the sample with a plurality of transduction particles capable of binding to the one or more target cells, wherein the plurality of transduction particles are (i) engineered to include a nucleic acid molecule formulated to cause the one or more target cells to produce a plurality of reporter molecules, (ii) formulated to bind to and deliver the nucleic acid molecules into the one or more target cells, and (iii) non-replicative; (b) maintaining the sample and the plurality of transduction particles under conditions sufficient to express the plurality of reporter molecules when the one or more target cells are present in the sample; (c) receiving a plurality of signal data points, each associated with a quantity of the plurality of reporter molecules, wherein the plurality of signal data points are indicative of the presence of the one or more target cells in the sample; (d) generating a first curve using the plurality of signal data points; (e) analyzing the first curve by calculating the following parameters based on the first curve: Area Under Curve (AUC); Area Under Peak (A2); Area Ratio; Global Maximum Intensity (globalmaxRLU); and Relative Variation (Rvar); and (f) comparing Area Ratio and Rvar and applying a linear threshold to identify a set of positive signal data points, wherein said set of positive signal data points reflect the presence of the one or more target cells in the sample. In some embodiments, the method further comprises analyzing the first curve by further calculating the following parameters based on the first curve: Area Under Curve (AUC); Area Under Peak (A2); Global Maximum Intensity (globalmaxRLU); Relative Variation (Rvar); Signal to Noise Ratio (S2N); Coefficient of Variation (CV); Spike Detection; Peak Position; Exponential Slope (eSlope); Area Ratio; Center of Mass (CM); and Relative Area (rArea). In some embodiments the method further comprises the step of generating a second curve using the set of positive signal data points and comparing rArea and S2N for the second curve to identify a revised set of positive signal data points, wherein said revised set of positive signal data points reflects the presence of the one or more target cells in the sample. In some embodiments, the method further comprises the step of comparing DeltaA2A and CM and applying a further linear threshold to identify a refined set of positive signal data points that reflect the presence of one or more target cells in the sample. In some embodiments, rArea=A2/(maximum in peak region). In some embodiments, Area Ratio=A2/AUC and Rvar is $$Rvar = \frac{\sum_{i=1}^{n-1} |nRLU_{i+1} - nRLU_i|}{\max(RLU)}, \text{ if } \max(RLU) > 0.$$

In some embodiments, the linear threshold is A2AInt+Rvar*A2ASlp, wherein A2AInt is an intercept of a threshold line for A2A vs. Rvar; Rvar is $$Rvar = \frac{\sum_{i=1}^{n-1} |nRLU_{i+1} - nRLU_i|}{\max(RLU)}, \text{ if } \max(RLU) > 0$$

and A2ASlp is a slope of the threshold line for A2A vs. Rvar. In certain embodiments, the method further comprises applying a linear threshold of rAreaInt+S2N*rAreaSlp. In some embodiments, AUC is calculated using a trapezoidal method. In some embodiments, A2 is defined over a fixed time interval. In certain embodiments, the time interval ranges from −0.10 seconds to 10.0 seconds. In some embodiments, A2 is defined over a variable time interval. In certain embodiments, the time interval is variable between −0.25 seconds <selected peak time in seconds <+2.00 seconds. In some embodiments, the method is used to detect antibiotic resistance in the sample.

Also provided is a computer-implemented method of detecting one or more target cells present in a sample, the method comprising, in a computer system: (a) receiving a plurality of signal data points, each associated with a quantity of the plurality of reporter molecules, wherein the plurality of signal data points are indicative of the presence of the one or more target cells in the sample; (b) generating a first curve using the plurality of signal data points; (c) analyzing the first curve by calculating the following parameters based on the first curve: Area Under Curve (AUC); Area Under Peak (A2); Area Ratio; Global Maximum Intensity (globalmaxRLU); and Relative Variation (Rvar); and (d) comparing Area Ratio and Rvar and applying a linear threshold to identify a set of positive signal data points, wherein said set of positive signal data points reflect the presence of the one or more target cells in the sample. In some embodiments, the method further comprises analyzing the first curve by further calculating at least one of the following parameters based on the first curve: Signal to Noise Ratio (S2N); Coefficient of Variation (CV); Spike Detection; Peak Position; Exponential Slope (eSlope); Center of Mass (CM); and Relative Area (rArea). In some embodiments, the method further comprises analyzing the first curve by further calculating the following parameters based on the first curve: Area Under Curve (AUC); Area Under Peak (A2); Global Maximum Intensity (globalmaxRLU); Relative Variation (Rvar); Signal to Noise Ratio (52N); Coefficient of Variation (CV); Spike Detection; Peak Position; Exponential Slope (eSlope); Area Ratio; Center of Mass (CM); and Relative Area (rArea). In some embodiments the method further comprises the step of generating a second curve using the set of positive signal data points and comparing rArea and S2N for the second curve to identify a revised set of positive signal data points, wherein said revised set of positive signal data points reflects the presence of the one or more target cells in the sample. In some embodiments, the method further comprises the step of comparing DeltaA2A and CM and applying a further linear threshold to identify a refined set of positive signal data points that reflect the presence of one or more target cells in the sample. In some embodiments, rArea=A2/(maximum in peak region). In some embodiments, Area Ratio=A2/AUC and Rvar is $$Rvar = \frac{\sum_{i=1}^{n-1} |nRLU_{i+1} - nRLU_i|}{\max(RLU)}, \text{ if } \max(RLU) > 0.$$

In some embodiments, the linear threshold is A2AInt+ Rvar*A2ASlp, wherein A2AInt is an intercept of a threshold line for A2A vs. Rvar; Rvar is $$Rvar = \frac{\sum_{i=1}^{n-1} |nRLU_{i+1} - nRLU_i|}{\max(RLU)}, \text{ if } \max(RLU) > 0$$

and A2ASlp is a slope of the threshold line for A2A vs. Rvar. In certain embodiments, the method further comprises applying a linear threshold of rAreaInt+S2N*rAreaSlp. In some embodiments, AUC is calculated using a trapezoidal method. In some embodiments, A2 is defined over a fixed time interval. In certain embodiments, the time interval ranges from −0.10 seconds to 10.0 seconds. In some embodiments, A2 is defined over a variable time interval. In certain embodiments, the time interval is variable between −0.25 seconds <selected peak time in seconds <+2.00 seconds. In some embodiments, the method is used to detect antibiotic resistance in the sample.

In another aspect a system configured to detect one or more target cells present in a sample is provided, the system comprising:
(a) a container defining a fixed volume within which a sample can be disposed,
(b) a reagent module defining a fixed volume within which one or more reagents can be disposed, the one or more reagents comprising a plurality of transduction particles capable of binding to the target cells, wherein the plurality of transduction particles are (i) engineered to include a nucleic acid molecule, (ii) formulated to cause the one or more target cells to produce a plurality of detectable reporter molecules, and (iii) non-replicative;
(c) a detector comprising an optical detection subsystem and/or an electrical detection subsystem, the detector being configured to detect the plurality of detectable reporter molecules; and
(d) a processor operably connected to the detector and configured to perform a computer-implemented method comprising:
(i) receiving a plurality of signal data points, each associated with a quantity of the plurality of reporter molecules, wherein the plurality of signal data points are indicative of the presence of the one or more target cells in the sample;
(ii) generating a first curve using the plurality of signal data points;
(iii) analyzing the first curve by calculating the following parameters based on the first curve: Area Under Curve (AUC); Area Under Peak (A2); Area Ratio; Global Maximum Intensity (globalmaxRLU); and Relative Variation (Rvar); and
(iv) comparing Area Ratio and Rvar and applying a linear threshold to identify a set of positive signal data points, wherein said set of positive signal data points reflect the presence of the one or more target cells in the sample.

In some embodiments, the method further comprises analyzing the first curve by further calculating at least one of the following parameters based on the first curve: Signal to Noise Ratio (S2N); Coefficient of Variation (CV); Spike Detection; Peak Position; Exponential Slope (eSlope); Center of Mass (CM); and Relative Area (rArea). In some embodiments, the method further comprises analyzing the first curve by further calculating the following parameters based on the first curve: Area Under Curve (AUC); Area Under Peak (A2); Global Maximum Intensity (globalmaxRLU); Relative Variation (Rvar); Signal to Noise Ratio (S2N); Coefficient of Variation (CV); Spike Detection; Peak Position; Exponential Slope (eSlope); Area Ratio; Center of Mass (CM); and Relative Area (rArea). In some embodiments the method further comprises the step of generating a second curve using the set of positive signal data points and comparing rArea and S2N for the second curve to identify a revised set of positive signal data points, wherein said revised set of positive signal data points reflects the presence of the one or more target cells in the sample. In some embodiments, the method further comprises the step of comparing DeltaA2A and CM and applying a further linear threshold to identify a refined set of positive signal data points that reflect the presence of one or more target cells in the sample. In some embodiments, rArea=A2/(maximum in peak region). In some embodiments, Area Ratio=A2/AUC and Rvar is $$Rvar = \frac{\sum_{i=1}^{n-1} |nRLU_{i+1} - nRLU_i|}{\max(RLU)}, \text{ if } \max(RLU) > 0.$$

In some embodiments, the linear threshold is A2AInt+ Rvar*A2ASlp, wherein A2AInt is an intercept of a threshold line for A2A vs. Rvar; Rvar is $$Rvar = \frac{\sum_{i=1}^{n-1} |nRLU_{i+1} - nRLU_i|}{\max(RLU)}, \text{ if } \max(RLU) > 0$$

and A2ASlp is a slope of the threshold line for A2A vs. Rvar. In certain embodiments, the method further comprises applying a linear threshold of rAreaInt+S2N*rAreaSlp. In some embodiments, AUC is calculated using a trapezoidal method. In some embodiments, A2 is defined over a fixed time interval. In certain embodiments, the time interval ranges from −0.10 seconds to 10.0 seconds. In some embodiments, A2 is defined over a variable time interval. In certain embodiments, the time interval is variable between −0.25 seconds <selected peak time in seconds <+2.00 seconds. In some embodiments, the method is used to detect antibiotic resistance in the sample.

A better understanding of the nature and advantages of embodiments of the present invention may be gained with reference to the following detailed description and the accompanying drawings.

BRIEF DESCRIPTION OF THE DRAWINGS

FIGS. 4A-4C are flowcharts illustrating the method described herein. FIG. 4A provides a full overview of the method while FIG. 4B illustrates further details of the data analysis portion of the method. FIG. 4C provides additional details regarding the data analysis portion of the method.

DETAILED DESCRIPTION

Figure 1:
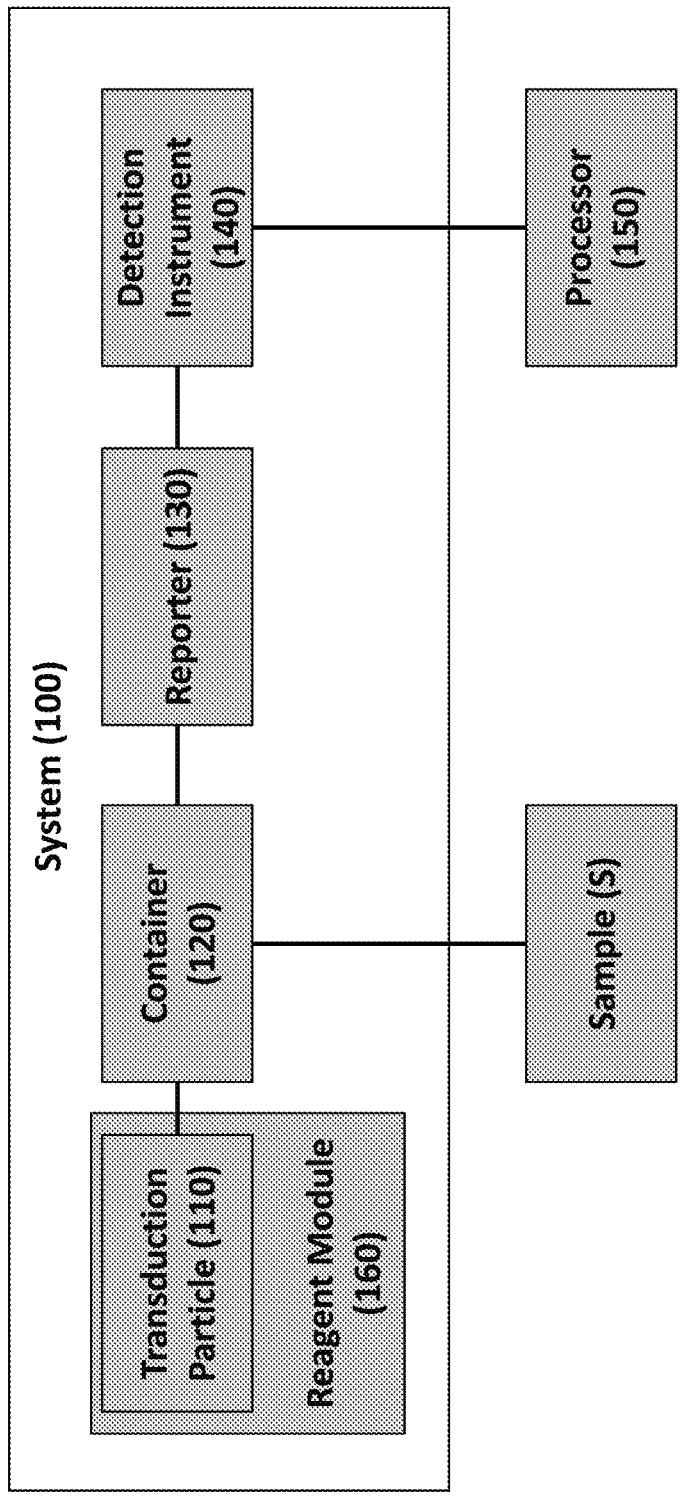
FIG. 1 is a block drawing of an instrument configured to analyze a sample as described herein.

Embodiments can detect the presence of one or more target cells in a sample based on a flash and glow reaction. Conventional methods detect false positive and negative samples, leading to inaccurate results which could negatively impact treatment decisions. The methods and systems described herein provide a mechanism to consistently and accurately identify target cells that were not correctly detected using conventional logic.

Unless otherwise defined herein, scientific and technical terms used herein have the meanings that are commonly understood by those of ordinary skill in the art. Further, unless otherwise required by context, singular terms include pluralities and plural terms include the singular. The articles "a" and "an" are used herein to refer to one or to more than one (i.e., to at least one) of the grammatical object of the article. By way of example, "an element" means one element or more than one element.

The terms "detect," "detecting," "detection," and similar terms are used in this application to broadly refer to a process of discovering or determining the presence or an absence, as well as a degree, quantity, or level, or probability of occurrence of something. For example, the term "detecting" when used in reference to a target cells, can denote discovery or determination of the presence, absence, level or quantity, as well as a probability or likelihood of the presence or absence of the target cell. It is to be understood that the expressions "detecting presence" and related expressions include qualitative and quantitative detection.

The terms "nucleic acid," "polynucleotide," and "oligonucleotide" refer to polymers of nucleotides (e.g., ribonucleotides or deoxyribo-nucleotides) and includes naturally-occurring (adenosine, guanidine, cytosine, uracil and thymidine), non-naturally occurring, and modified nucleic acids. The term is not limited by length (e.g., number of monomers) of the polymer. A nucleic acid may be single-stranded or double-stranded and will generally contain 5'-3' phosphodiester bonds, although in some cases, nucleotide analogs may have other linkages. Monomers are typically referred to as nucleotides. The term "non-natural nucleotide" or "modified nucleotide" refers to a nucleotide that contains a modified nitrogenous base, sugar or phosphate group, or that incorporates a non-natural moiety in its structure. Examples of non-natural nucleotides include dideoxynucleotides, biotinylated, aminated, deaminated, alkylated, benzylated and fluorophor-labeled nucleotides.

As used herein, a target cell is a bacterium, including but not limited to, e.g., *Escherichia, Mycobacterium, Staphylococcus, Listeria, Clostridium, Enterococcus, Streptococcus, Enterobacteriaceae, Helicobacter, Rickettsia, Haemophilus, Xenorhabdus, Acinetobacter, Bordetella, Pseudomonas, Aeromonas, Actinobacillus, Pasteurella, Vibrio, Legionella, Bacillus, Calothrix, Methanococcus, Stenotrophomonas, Chlamydia, Neisseria, Salmonella, Shigella, Campylobacter* and *Yersinia*. The following target cells are specifically contemplated:

*Staphylococcus*, and in particular, methicillin-resistant or methicillin-susceptible *Staphylococcus aureus* (MRSA and MSSA, respectively).

Enterobacteriaceae, and in particular, carbapenem-resistant Enterobacteriaceae (CRE) or carbapenemase-producing Enterobacteriaceae (CPE).

*Pseudomonas aeruginosa*, a common gram-negative bacterium that can cause disease in plants and animals, including humans. *P. aeruginosa* is a multidrug resistant pathogen recognized for its ubiquity, its intrinsically advanced antibiotic resistance mechanisms, and its association with serious illnesses—especially hospital-acquired infections such as ventilator-associated pneumonia and various sepsis syndromes.

*Acinetobacter baumannii*, a coccobacillus Gram-negative bacterium, that is an opportunistic pathogen in humans, affecting people with compromised immune systems, and is becoming increasingly important as a hospital-derived (nosocomial) infection. *A. baumannii* has also been identified as an ESKAPE pathogen (*Enterococcus faecium, Staphylococcus aureus, Klebsiella pneumoniae, Acinetobacter baumannii, Pseudomonas aeruginosa*, and *Enterobacter* species), a group of pathogens with a high rate of antibiotic resistance that are responsible for the majority of nosocomial infections.

Coagulase-negative staphylococci are common inhabitants of the skin and mucous membranes. *S. epidermidis* is the most prevalent species, accounting for approximately 60-70% of all coagulase-negative staphylococci on the skin. Coagulase-negative staphylococci are frequently associated with nosocomial infections. Conversely, due to their ubiquity on the skin, they are the most frequent contaminants of blood cultures often complicating the interpretation of these tests. Resistance to penicillin among the coagulase-negative staphylococci approaches 90 to 95 percent. Resistance to methicillin and semisynthetic penicillins has been observed in more than 80 percent of CoNS isolates; these isolates are often resistant to multiple classes of antibiotics in addition to beta-lactams.

Vancomycin-resistant Enterococci (VRE) and Fluoroquinolone-resistant Enterobacteriaceae are (FRE) are specific types of antimicrobial-resistant bacteria that are resistant to vancomycin and fluoroquinoline, respectively, common treatment options for bacteria of these types.

It can be difficult to discriminate between target cells, e.g., between MRSA and MSSA or between CPE or CRE. Some tests for determining whether a specific target cell is present in a sample involve a flash reaction, e.g., as described in PCT publications WO2014/160418, WO2014/164768, and WO2015/164746 and U.S. Publication No. 20150218613. Such flash signals can be detected by a detector, e.g., as signal data points detected at various times, and flash signals can occur in numerous reactions of various analytes, including, for example, live cell luminescence assays.

In some embodiments, the presence of a target cell in a sample can be detected based on signals resulting from a flash reaction involving a target cell in the sample and an activation reagent. In a specific example, a system is designed for detecting the presence of a target cell, e.g., CRE, CPE, MRSA, or MSSA, via a luminescence assay (an example including an activation reagent). The assay can employ a first reagent that causes viable target cells to produce a luminescence signal when activated via a second reagent. A detector (e.g., a photomultiplier tube-based (PMT) detector) is employed for collecting data. The collected data can be analyzed to distinguish the presence vs. absence of the target cell based on characteristics of the data collected. The analysis can provide an accurate measurement of the sample for the presence of the analyte. Parameters of the analysis can be chosen based on reference data from samples known to be positive and negative for the target cell, respectively, such that the results produce a desired sensitivity and specificity with respect to the reference data.

The reference data may be identified as positive/negative for the target cell based on any suitable reference assay, including those accepted as standards. For example, the reference data is determined to be known positive/negative for MRSA based on an enriched culture method for MRSA detection as described in FDA Draft Document—Establishing the Performance Characteristics of Nucleic Acid-Based In vitro Diagnostic Devices for the Detection and Differentiation of Methicillin-Resistant *Staphylococcus aureus* (MRSA) and *Staphylococcus aureus* (SA); Issued on Jan. 5, 2011, which is incorporated by reference. Such a test has high accuracy, but is time-consuming and costly to run, and thus not practical in many instances.

In some embodiments, the system described in PCT publication WO 2014/164768 can be employed using the consumable described in PCT publication WO 2015/164746 and running the target cell assay described in PCT publication WO 2014/160418 that describes the assay and performance; all of these publications are incorporated by reference in their entirety.

Systems, devices and methods for detecting and identifying target cells or other analytes can include a transduction particle, which can identify and bind to the target cell and deliver into the target cell an engineered nucleotide. As shown in the block diagram of FIG. 1, in some embodiments, a system 100 includes a genetically engineered transduction particle 110, a container 120, a reporter 130, a detection instrument 140, and a processor 150. In a specific embodiment, the particle 110 is disposed within a reagent module 160. The system 100 is configured to manipulate, handle and/or actuate the container 120 and/or the detection instrument 140 such that the transduction particle 110 can, when mixed with a sample S that contains a particular target, produce the reporter 130. In this manner, the system 100 and methods associated therewith can be thought of as a "switchable" assay, meaning that no amount of the reporter 130 is present in the sample until the conditions (e.g., the presence of the target cell) are such that the reporter 130 is produced. Detection instrument 140 can be a photomultiplier tube (PMT). The PMT detects photons from the reactions to provide a signal over time.

The transduction particle 110 can be any suitable particle capable of delivering reporter DNA and/or RNA into a target cell. For example, in some embodiments, the transduction particle can be derived from a bacteriophage, or can be a non-biologically derived vector that is capable of introducing nucleic acid molecules into the target bacteria in the sample S. The transduction particle 110 is further engineered and/or configured to carry an engineered molecule, for example, recombinant DNA, RNA, nucleotide, plasmid, ribozyme, aptamer, and/or protein. In some embodiments, the transduction particle 110 does not contain any DNA from the viral vector (e.g., bacteriophage) from which it was derived. Similarly stated, in some embodiments, the transduction particle is a viral vector devoid of a wild-type DNA capable of exhibiting wild-type viral functions associated with the virus from which the viral vector is derived.

In some embodiments, the transduction particle 110 is incapable of replicating via either the lytic or lysogenic cycle. By eliminating all forms of replication from the transduction particle, the target cells will be maintained (i.e., not destroyed, killed or lysed) during the production of the reporter molecules, thereby improving the accuracy and reliability of the methods used therewith. In particular, because wild-type viral functions of viral particles can exhibit lysogenic replication and require the capability for lytic replication, attempts to suppress the replicative functions (e.g., the lytic cycle) may not provide sufficient certainty that the lytic cycle will not result in some population of assays.

The transduction particle 110 can be characterized by being associated with and/or specific to one or more target cells. Similarly stated, the transduction particle 110 is formulated to bind to and deliver a nucleic acid molecule into the target cell. For example, the transduction particle can be selected, engineered and/or produced to bind to any bacteria, e.g., *Escherichia, Mycobacterium, Staphylococcus, Listeria, Clostridium, Enterococcus, Streptococcus, Helicobacter, Rickettsia, Haemophilus, Xenorhabdus, Acinetobacter, Bordetella, Pseudomonas, Aeromonas, Actinobacillus, Pasteurella, Vibrio, Legionella, Bacillus, Calothrix, Methanococcus, Stenotrophomonas, Chlamydia, Neisseria, Salmonella, Shigella, Campylobacter* and *Yersinia*. In a specific embodiment, the target cell is Enterobacteriaceae, and in particular, carbapenem-resistant Enterobacteriaceae (CRE) or carbapenemase-producing Enterobacteriaceae (CPE). In a further embodiment, the target cell is *Staphylococcus*, and in particular, methicillin-resistant or methicillin-susceptible *Staphylococcus aureus* (MRSA and MSSA, respectively) and the transduction particle is selected, engineered and/or produced to bind to MRSA and/or MSSA.

The transduction particle 110 can be further produced and/or engineered to contain genes and/or a nucleic acid molecule for expressing a reporter 130 that can be detected (e.g., via the instrument 140). The reporter 130 can be any one of a bacterial luciferase, an eukaryotic luciferase, a fluorescent protein (e.g., GFP, etc.), an enzyme suitable for colorimetric detection (e.g., horseradish peroxidase) a protein suitable for immunodetection (e.g., protein A, etc.), a peptide or peptide tag suitable for immunodetection (e.g., 3.times.FLAG, etc.) and/or a nucleic acid that functions as an aptamer or that exhibits enzymatic activity. More particularly, the transduction particle 110 does not produce the reporter 130 autonomously and/or does not include the reporter 130. Instead, transduction particle 110 is configured to communicate an engineered nucleic acid molecule contained therein into the target cell, e.g., bacteria, such that the engineered nucleic acid molecule uses the natural transcription and translation functions of the bacteria DNA to produce the reporter 130. Thus, the reporter 130 can be thought of as a "switchable" reporter, meaning that no amount of the reporter 130 is present in the sample until the conditions (e.g., the presence of the target cell) are such that the reporter 130 is produced. In this manner, certain methods may involve no washing of non-bound reporter 130, no signal subtraction to account for initial quantities of reporter or the like. Thus, the system 100 and the methods associated therewith allows for the development of a homogeneous assay. Further, no temperature cycling may be required, and heating at a low temperature, for example 37 degrees Celsius, for a short time can be sufficient.

The reporter system formulated to cause the expression of the reporter 130 and any of the reporter systems disclosed herein can be developed for reporting on the presence of viable bacteria and/or target cells by incorporating into the non-replicative transduction particle 110 (or any of the other transduction particles disclosed herein) a reporter molecule under the control of a promoter. When this transduction particle 110 introduces the reporter system into a cell within the host range of the transduction particle 110, the promoter is able to drive the expression of the reporter molecule.

For example, a MSSA/MRSA reporter assay can be developed and/or performed using any suitable system. In such embodiments, a non-replicative transduction particle (e.g., the transduction particle 110) is developed from a *S. aureus*-specific bacteriophage, and the bacterial luciferase genes luxAB under the control of a constitutive promoter are incorporated. When this transduction particle introduces the reporter system into *S. aureus*, the constitutive promoter can express luxAB suitable for reporting on the presence of a viable *S. aureus*. If in addition, the antibiotic cefoxitin, or a similar antibiotic, is also added prior to or simultaneously with mixing the transduction particles with *S. aureus* cells, if the cells do not contain and express the mecA gene, no luxAB will be expressed in the assay, thus indicating that the cells are MSSA (i.e., sensitive to inhibition by cefoxitin). If, however, the cells do contain and express the mecA gene, luxAB will be expressed in the assay, thus indicating that the cells are MRSA (i.e., resistant to inhibition by cefoxitin).

Although described as being developed for reporting on the presence of viable bacteria, in other embodiments, the reporter 130 and any of the applicable reporter systems can be developed for reporting on the presence of target genes within target bacteria. In this system, a promoter-less reporter gene is placed downstream of a nucleic acid sequence that is homologous to a target gene sequence, and this reporter construct is incorporated into a non-replicative transduction particle. When the transduction particle introduces the reporter construct into a target cell, the reporter gene will not be expressed unless the target cell contains the target gene, and a homologous recombination event integrates the reporter gene within the target gene loci in the target cell such that the reporter gene becomes operatively linked to the target gene promoter within target cell.

In one such embodiment, a MRSA reporter system can be developed by incorporating into a *S. aureus*-specific non-replicative transduction particle (e.g., the transduction particle 110) a reporter construct consisting of a nucleic acid sequence that is homologous to the mecA gene upstream of promoter-less bacterial luciferase genes, luxAB. When the transduction particle introduces the reporter construct into a target *S. aureus* cell, the reporter gene will not be expressed unless the target cell contains the target mecA gene and a homologous recombination event integrates the luxAB genes within the mecA gene loci in the target cell such that the reporter gene becomes operatively linked to the mecA gene promoter within target cell.

In some embodiments, transduction particle 110, the nucleic acid molecule contained within the transduction particle 110 and/or the reporter systems associated therewith can include any of the portions of the recombinant bacteriophages shown and described in U.S. Patent Publication No. 2010/0112549, entitled "Microorganism Detection Method and Apparatus," filed as an International Patent Application on Apr. 18, 2008, which is incorporated herein by reference in its entirety.

The sample S can be any sample that possibly contains the target analyte, for example, human nasal swab, blood, urine, veterinary samples, food samples, and/or environmental samples. In some embodiments, the sample S can be a raw sample as obtained from the source that does not need any preparation, e.g., any separation or washing steps are not needed. Thus, the system 100 and the methods associated therewith can be homogeneous. In some embodiments, the sample S can include a low load of target cell (e.g., nasal swab for MRSA detection). When used with such samples, the system 100 and the methods associated therewith can include a heating and/or incubation period to promote cell replication, which results in higher production of the reporter molecules 130, for example, to generate a signal that is greater than a minimum signal threshold.

In other embodiments, the sample S can have a higher load of target cell (e.g., positive bacterial blood culture). In such cases, cell replication is not needed to produce a positive signal sufficient to identify the target cell. In some such embodiments, the sample can be maintained at a specific condition e.g., maintained at a temperature of greater than or equal to approximately room temperature, 25 degrees Celsius, or 37 degrees Celsius for a predefined time period e.g., less than approximately 4 hours. In such embodiments, the temperature and time period at which the sample S is maintained are such that the quantity of reporter molecules 130 produced is sufficient to generate a measurable signal, independent of cell replication. In such embodiments, the sample can be maintained at the predefined temperature for a longer time period, e.g., 6 hours, 8 hours, up to 18 hours, or even longer.

In some embodiments, the container 120 can contain a first reagent, for example, a bacterial nutrient or growth media (e.g., minimal essential media) and/or suitable buffer (e.g. Amies, PBS, TRIS, HEPES, etc) for maintaining the target cell in a viable state, promoting bacterial cell growth or the like. In some embodiments, an antibiotic, for example, cefoxitin can also be included in the first reagent, for example, when a viable cell assay is intended. A sample S containing the target cell can be added to container 120 followed by addition of the transduction particle 110 to container 120. If the target cells are present, the transduction particle 110 transfers the nucleic acid sequence contained therein into the target cell such that the nucleotide contained in the transduction particle 110 is integrated with the genes of the target cell, e.g., host bacteria.

In some embodiments, the container 120 is configured to fluidically isolate the sample S from a region outside the container 120. In such embodiments, the transduction particle 110 is maintained in fluidic isolation from the sample S before the transduction particle 110 is mixed therein. In some embodiments, the maintaining can include maintaining the sample S for a time period such that the quantity of the plurality of the reporter molecules 130 sufficient to produce the signal is produced independent from target cell replication. As described herein, mixing includes disposing the transduction particle 110 into the sample S while maintaining isolation between the region and the container 120.

In some embodiments, the container 120 can be configured to include an activation reagent that is formulated to react with the reporter molecules 130 to produce, catalyze and/or enhance the production of the signal. For example, the reporter molecule 130 can be luciferase, and the container 120 can be configured to contain an aldehyde reagent formulated to trigger, initiate and/or catalyze a luminescence reaction that can be detected by the production of the signal. In one implementation, a cap of container 120 can contain the activation reagent (e.g., in a blister) that is mixed with the transduced samples via actuation (e.g., popping the blister) by an instrument of system 100.

In various embodiments, the activation reagent can include a 6-carbon aldehyde (hexanal), a 13-carbon aldehyde (tridecanal) and/or a 14-carbon aldehyde (tetradecanal), inclusive of all the varying carbon chain length aldehydes therebetween. In some embodiments, the container 120 can be configured to maintain the activation reagent in fluidic isolation from sample S before being disposed into the sample S. In this manner the timing of the delivery of the activation reagent into the sample S can be controlled. In some embodiments, the system 100 can include a mechanism for adding the activation reagent at any suitable time and/or in any suitable manner to induce the detectable signal. For example, as described in more detail herein, in some embodiments, the system 100 and/or the container 120 can include a mechanism for conveying an activation reagent into the sample S at a predetermined velocity (or flow rate) to promote the desired level of mixing.

The instrument 140 can be any appropriate instrument to detect the reporter molecule 130 and/or a reaction catalyzed by the reporter molecule 130. For example, the instrument 140 can include optical (e.g. photomultiplier tubes, fluorometers, spectrometers, colorimetric detection on a lateral flow assay, imaging based detection, CCDs, luminescence detectors for detecting bioluminescence, colorimetric or fluorometric microarrays) and/or electrical detection means (e.g. electrochemical amperometric, potentiometric, conductometric, impedrometric, coulometric, and/or any other electrochemical sensors).

Instrument 140 is connected with processor 150 that analyzes the measured data. The connection can be wired or wireless. As an example of a wireless connection, a removable data storage device at instrument 140 can store the measured data, and the storage device can be removed and inserted into computer system 150.

In some embodiments, the system 100 and/or the methods associated therewith can be configured to be a rapid test that does not require any amplification of the target cells. Using the system 100 and the methods described herein, a relatively small time, for example, 1 hour, 2 hour, 3 hour or 4 hour, up to 18 hours can be needed for the target cell containing the nucleic acid sequence from the transduction particle 110 to produce a sufficient quantity of reporter molecules 130 that can be detected. In some embodiments, the system 100 can be configured to be a closed system after collection of sample S and/or addition of transduction particle 110. In a specific embodiment, the container is maintained in fluidic isolation from the external environment after the addition of the sample S. This can, for example, reduce chances of contamination. As described above, because the system 100 can accommodate raw sample, the system 100 and the methods associated therewith do not require any washing or fluid transfer steps away from the sample S. The system 100 can therefore be easy to operate, be rapid, inexpensive, and be easily automated. In some embodiments, the system 100 can be a platform system that can be configured to operate in various regimes, for example, viable cell reporting, gene reporting, measuring bacterial resistance and/or susceptibility to antibiotics, and/or bacterial toxin detection, etc.

Embodiments involve reactions that are of a flash type, and can also include later time region where a glow signal can be seen. Luminescence assays can come in many different types. Luminescence assays are a chemical or enzymatic reaction that use a substrate (activation reagent). In the case of the reporter molecule being bacterial luciferase (LuxAB), the substrate can be a fatty aldehyde (e.g. tridecanal). When the substrate is acted upon by the chemical or enzymatic reaction, light is given off as a by-product. The two main types of luminescence reactions are flash and glow. The flash luminescence reaction can occur quickly, e.g., in a matter of seconds or minutes, giving off a very bright signal. Whereas a glow luminescence assays can last for hours, but are typically not as bright as flash luminescence assays.

As described above, a flash signal can be produced by a sample when an activation reagent activates an analyte or a molecule generated from the analyte (e.g., a reporter molecule generated by bacteria in response to a transduction particle. But, a flash signal can be generated by other similar analytes, as well as the target analyte. For example, a flash signal is generated for MSSA and MRSA. This poses a problem for the discrimination analysis in classifying the sample as positive or negative for the target analyte.

Figure 2:
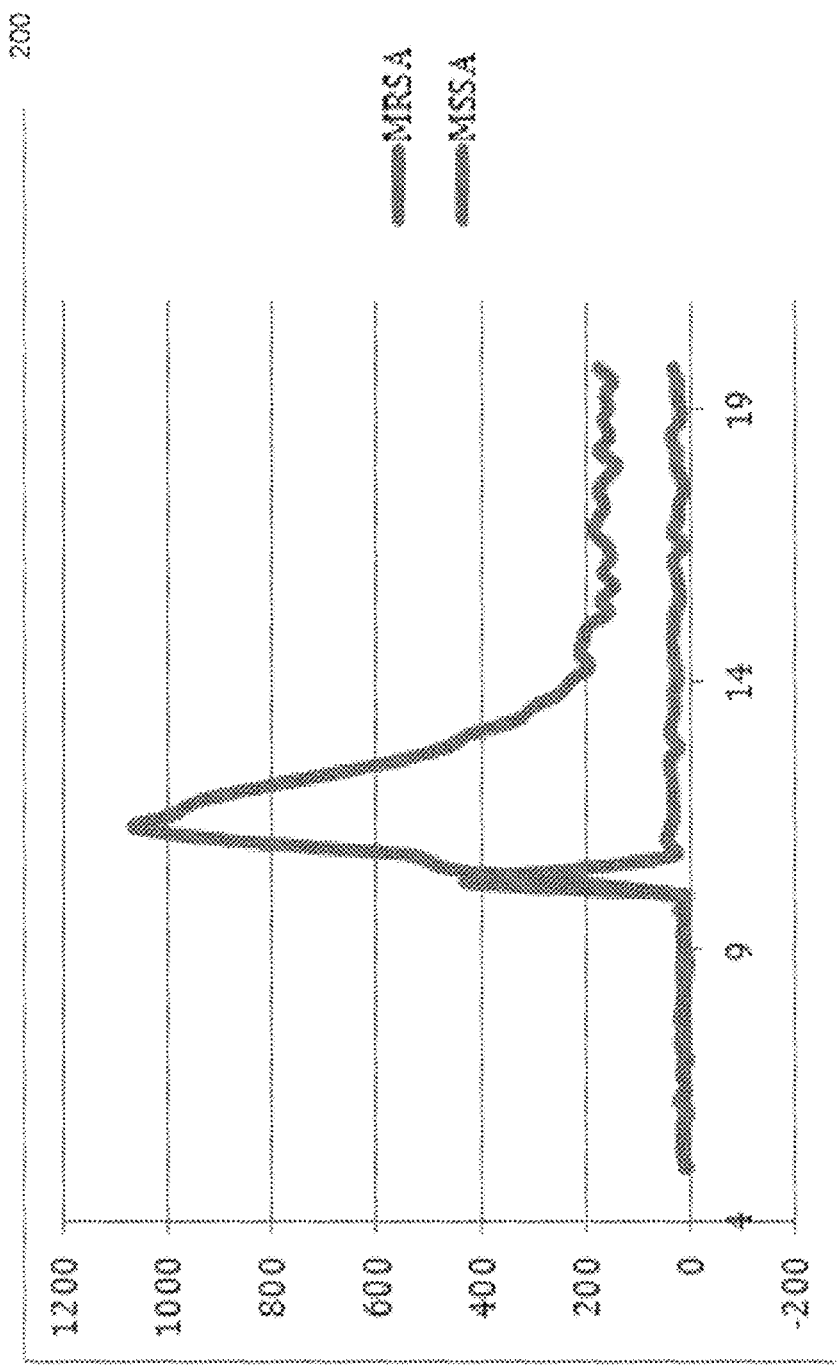
FIG. 2 is a typical plot of a luminescence signal for a sample subjected to a flash and glow reaction.

FIG. 2 shows a typical plot 200 of a MRSA signal and a MSSA signal from respective samples subjected to a flash and glow reaction. The horizontal axis corresponds to time. The vertical axis corresponds to a signal intensity measured by a detector (e.g., a PMT). The measured data includes baseline measurements (data collected before activation reagent is added) and substrate measurements (signal data collected after activation reagent is added). Such signals can result for other analytes besides MRSA.

Figures 3A, 3B, 3C, 3D, 3E, 3F:
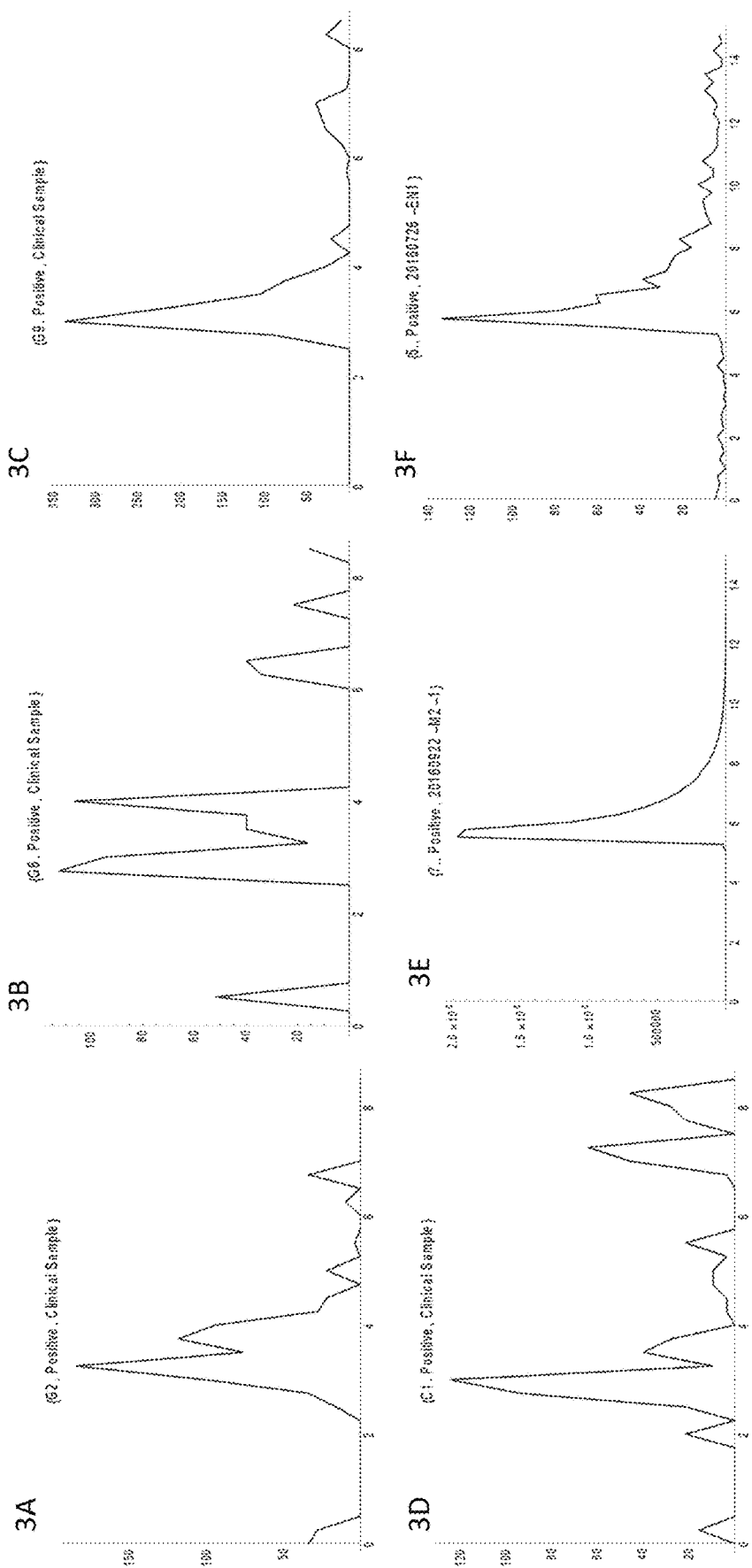
FIGS. 3A-3P are representative positive and negative curves without additional data analysis.
Figures 3G, 3H, 3I, 3J, 3K, 3L:
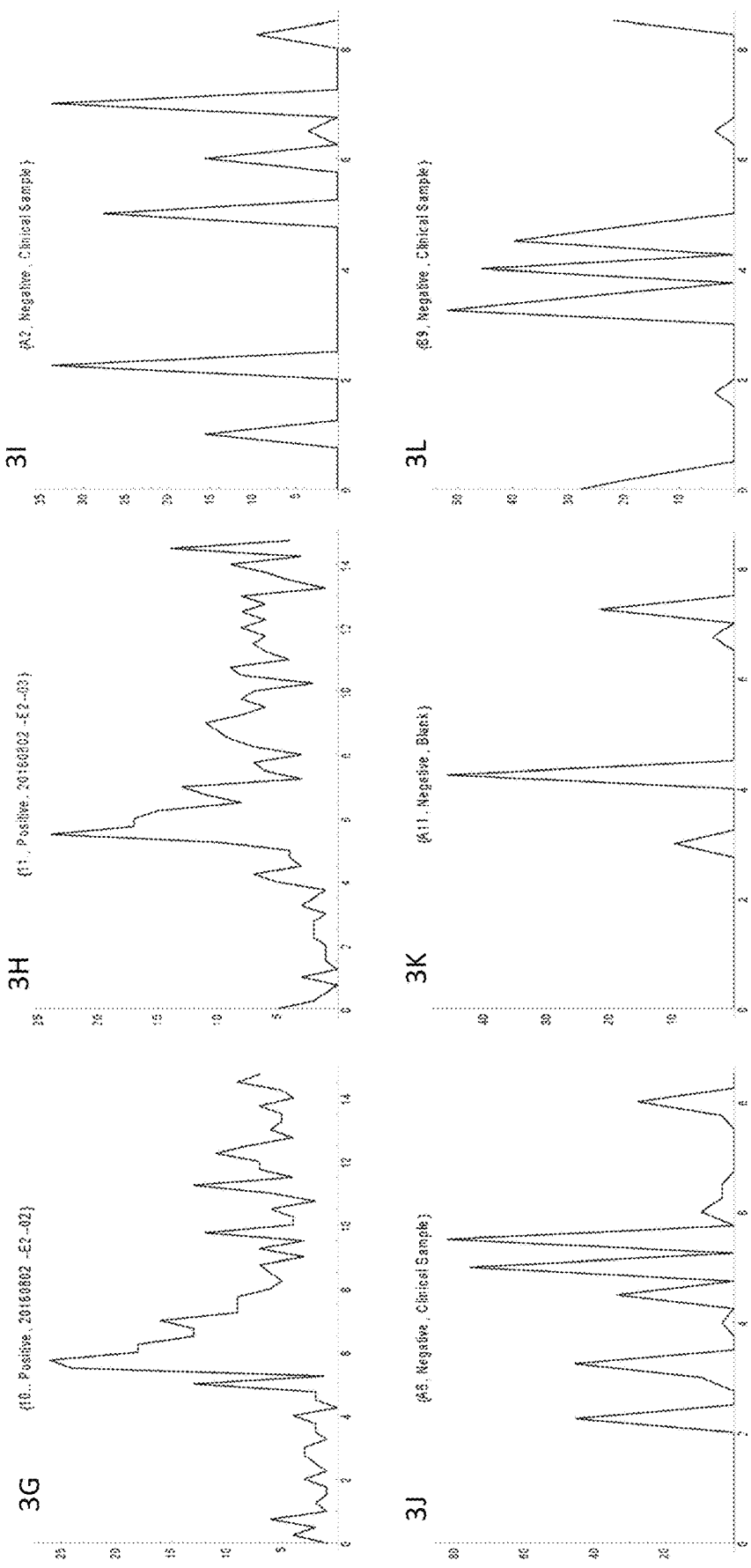
Figures 3M, 3N, 3O, 3P:
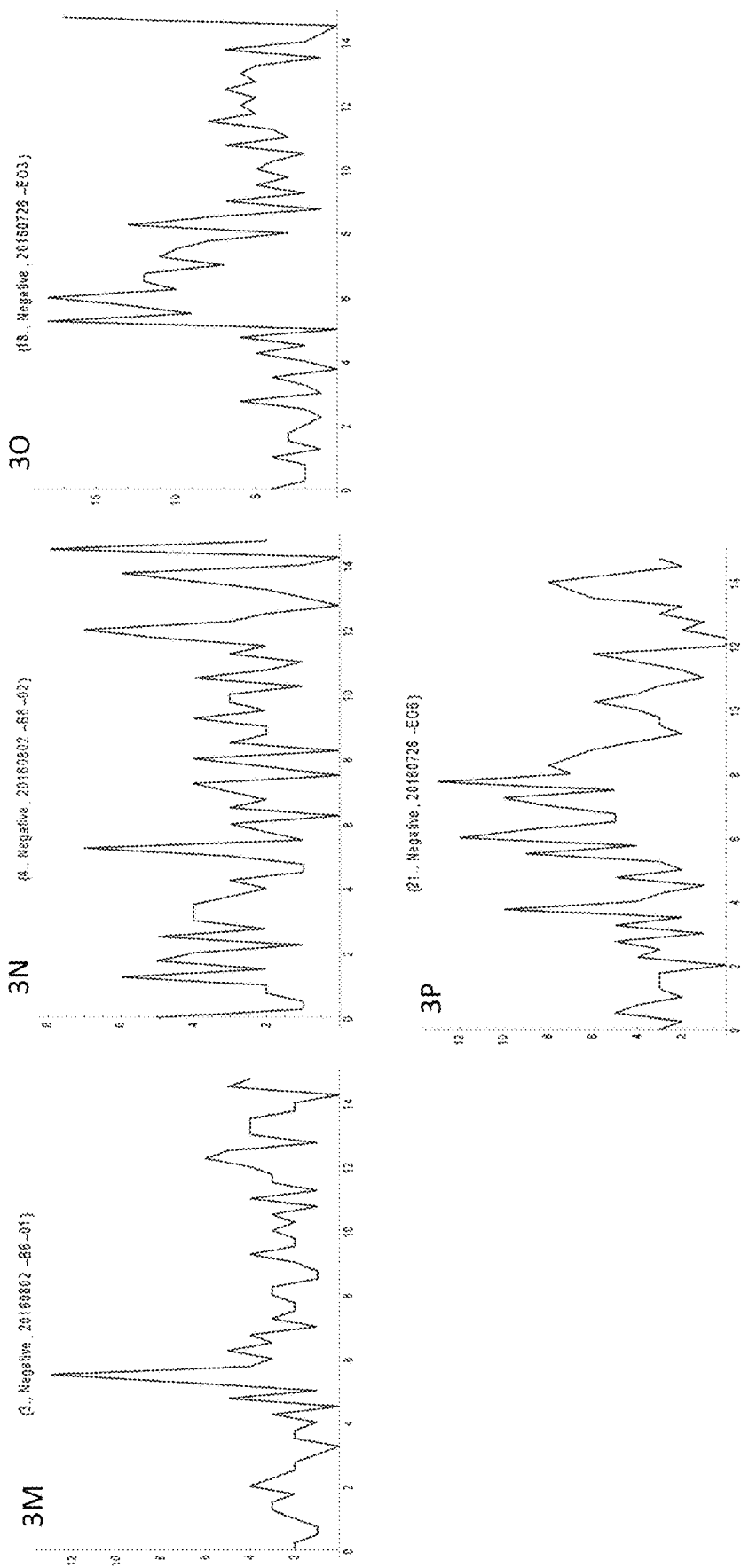

Although the two signals shown have different maximum values (about 400 for MSSA and about 1050 for MRSA), the maximum values can be much closer. Some MSSA samples can even have a higher maximum signal value (peak) than the maximum for some MRSA samples. Positive signals can have a wide range from very low to high peaks. This noise of similar signals can cause problems for differentiating between positive and negative samples. Thus, just using a maximum value provides too many false positives, e.g., below a desired sensitivity and specificity, as is shown below. Further, the peak can occur at various time points. Examples of representative positive and negative curves without additional data analysis are shown in FIGS. 3A-3P.

To address these difficulties, embodiments can use multiple signal values over time, and not just a single value, so as to analyze a range of kinetics of the signal data. Embodiments can also analyze a curvature of a signal around its peak, as a way to differentiate between positive and negative samples. Such techniques can focus on differentiating signals that are very close to each other so as to provide a desired sensitivity and specificity. Such close data is now discussed.

Figure 4C:
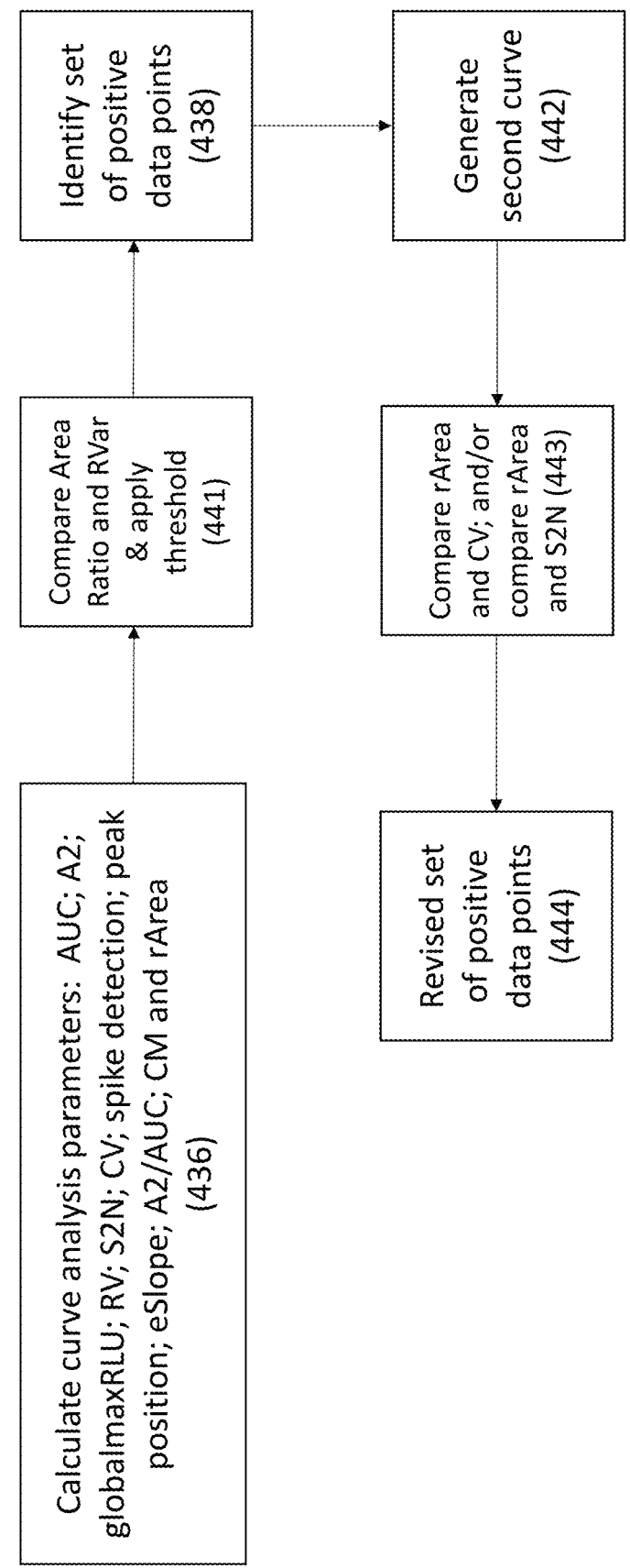

FIGS. 4A-4C illustrate one embodiment of the method described herein. First, as described above, a sample suspected of including one or more target cells is mixed with a plurality of transduction particles capable of binding to the one or more target cells (410). The plurality of transduction particles have the following properties: (i) they are engineered to include a nucleic acid molecule formulated to cause the one or more target cells to produce a plurality of reporter molecules, (ii) the plurality of transduction particles are formulated to bind to and deliver the nucleic acid molecules into the one or more target cells, and (iii) the particles are non-replicative. The mixture formed in the first step is maintained under conditions sufficient to express the plurality of reporter molecules when the target cells are present in the sample (420). The reporter molecules generate a detectable signal (430), e.g., via the emission of a luminescence signal, wherein each data point is associated with a quantity of reporter molecules indicative of the presence of the one or more target cells in the sample. The signal generated is subjected to one or more data analysis steps (440) and the data set is then used to determine if the sample includes the one or more target cells (450).

The one or more signal analysis steps are illustrated in more detail in FIG. 4B. The detectable signal generated by the plurality of reporter molecules is received by a processor as a set of one or more signal data points (432) that are used to generate a first curve (434) in which signal intensity is plotted against time. The first curve is analyzed by calculating a set of curve analysis parameters (436), and one or more of the parameters are used to identify the positive signal data points that reflect the presence of the one or more target cells in the sample (438).

Various curve analysis parameters can be calculated and used to identify positive signal data points. For example, the curve analysis parameters include, but are not limited to, one or more of the following:

(a) Area Under Curve (AUC). The AUC is defined as the total area under the curve, and it can be determined, for example, using the trapezoidal rule which approximates the region under the curve as a trapezoid and calculates its area. Other methods are known in the art to calculate AUC, including but not limited to Simpson's rule, as described in http://mathworld.wolfram.com/SimpsonsRule.html. See also, Abramowitz, M. et al. (Eds.). Handbook of Mathematical Functions with Formulas, Graphs, and Mathematical Tables, 9th printing. New York: Dover, p. 886, 1972; Horwitz, A. "A Version of Simpson's Rule for Multiple Integrals." J. Comput. Appl. Math. 134, 1-11, 2001.

(b) Area Under Peak (A2). Under ideal circumstances, flash and glow assays produce a luminescence response (when positive) including a sharp exponential increase of intensity at a defined time, followed by a slow exponential decay. This is illustrated, for example, in FIG. 2. A2 is defined as the area under the peak within a predetermined time interval. The time interval can be fixed or variable. For example, the time interval can be fixed in the range from −0.10 seconds to 7.0 seconds, particularly, from 2.0-6.5 seconds, 2.0-4.0 seconds, or more particularly, from 2.75-3.25 seconds. The time interval can also be fixed in the range of from 5.0-7.0 seconds, e.g., 5.25-6.25 seconds. Alternatively, the time interval can be variable, e.g., between −0.25 seconds <selected peak time in seconds <+2.00 seconds, or between −0.25 seconds <selected peak time in seconds <+1.00 seconds.

(c) Global Maximum Intensity (globalmaxRLU). GlobalmaxRLU is the maximum luminescence signal over all time points. RLU is the relative luminescence signal based on raw data and nRLU is the raw signal after passing the signal through a Hampel filter, which is used to detect and remove outliers.

(d) Relative Variation (Rvar). Rvar is the sum of the absolute value differences between adjacent signals divided by the maximum luminescence of the entire signal. A large RV is indicative of increased noise. This parameter is one representation of the noise in the signal. Mathematically, RV=sum(|RLU(n+1)−RLU(n)|)/globalmaxRLU, wherein RLU is a relative luminescence signal and RLU(n) is RLU at time point n.

(e) Signal to Noise Ratio (S2N). S2N is the maximum luminescence signal in the peak region divided by the standard deviation of the luminescence signal outside the peak region. Mathematically, S2N is peak_region_globalmaxRLU/stdev(RLU outside peak region), wherein peak_region_globalmaxRLU is a time interval corresponding to a peak region of the first curve and stdev(RLU outside peak region) is a time interval preceding and following peak_region_globalmaxRLU.

(f) Coefficient of Variation (CV). CV is the standard deviation of the luminescence signal outside the peak region divided by the mean luminescence signal in the peak. CV is another representation of noise in the signal. A large CV is indicative of increased noise. CV=stdev(RLU outside peak region)/mean(RLU peak region), wherein RLU is a relative luminescence signal, RLU outside peak region is a relative luminescence signal outside of the peak region, and RLU peak region is a relative luminescence signal in the peak region.

(g) Spike Detection. It is important to differentiate the presence of spikes in the peak region from true signals. If tm is the time of the spike, a spike is then defined as having the luminescence signal equal to zero on either the adjacent left or right side, wherein the other adjacent side has either a 90% drop in luminescence signal relative to the peak or the subsequent time point has a 95% drop in luminescence signal relative to the peak. Mathematically, RLU[tm−1]=0 and (RLU[tm+1]≤(0.01−0.4)*RLU[tm] or RLU[tm+2]≤(0.001-0.3)*RLU[tm]), RLU[tm+1]=0 and (RLU[tm−1]≤(0.1)*RLU[tm] or RLU[tm−2]≤(0.001−0.3)*RLU[tm]), RLU[tm−1]=0 and (RLU[tm+1]≤(0.01−0.4)*RLU[tm] or RLU[tm+2]≤(0.05)*RLU[tm]), or RLU[tm+1]=0 and (RLU[tm−1]≤(0.1)*RLU[tm] or RLU[tm−2]≤(0.05)*RLU[tm]), wherein RLU is a relative luminescence signal, tm is a time corresponding to a spike in the first curve, and *RLU[tm] is the relative luminescence signal of the spike.

(h) Peak Position. In order for a peak to be considered positive, it should be located within a fixed set of time points. If the peak is outside of this region, it is considered negative. In one embodiment, the fixed set comprises 2.75-3.25 seconds. In an alternative embodiment, the fixed set comprises 5.25-6.25 seconds. However, the skilled artisan will readily appreciate that the set of time points can be empirically determined based on the specific needs of the operator and the specifications of the system in which the sample is analyzed.

(i) Exponential Slope (eSlope). Assuming that the peak is in the allowable peak range, the luminescence signal will typically undergo an exponential decay according to the following expression:

$A*\text{Exp}[-B*(t-t\text{max})]$, where $t\text{max}$ is the time of the peak, and $B$ is the eSlope.

If the eSlope exceeds a given threshold, then the curve is called negative.

(j) Area Ratio (A2A; A2/AUC). A2 and AUC are used as the area ratio, i.e., A2/AUC, so that machine to machine variability is minimized.

(k) Relative Area (rArea). In addition to or instead of calculating the Area Ratio (j), Relative Area is useful in curve positive/negative determination. Relative Area=globalmaxRLU/AUC, is also dimensionless, so that machine to machine variability is minimized. In a specific embodiment, rArea=A2/maxSignal in the peak region.

(l) DeltaA2A. The point on the A2A v. Rvar plot minus the threshold line A2AInt+Rvar*A2ASlp.

(n) MaxSignal. Maximum signal in peak region (Interval 2).

(o) Center of Mass (CM). Center of Mass; CM=sum(RLU (t)×t)/sum(RLU(t)). A plot of DeltaA2A vs. CM can be used to determine the CM threshold and curves with a CM>CMMax and MaxSignal >minRLU and ZTest 0 are called invalid.

As shown in FIG. 4C, once the curve analysis parameters are determined (436), the curve is further evaluated by comparing Area Ratio and Rvar and applying a linear threshold (441) to identify the positive signal data points (438). In addition or as an alternative, the data can be further evaluated by generating a second curve using the positive signal data points (442), comparing rArea and CV for the second curve (443), and generating a revised set of positive signal data points (444). Additionally or alternatively, the data can also be evaluated by generating a second curve using the positive signal data points and comparing rArea and S2N for the second curve and generating a revised set of positive signal data points.

As illustrated in the Examples that follow, using the methods described herein one can detect positive samples with a high degree of sensitivity and specificity. In particular, by analyzing the data as described above, i.e., generating a curve based on the signal data points, calculating the assay curve parameters based on the curve, and comparing the curve parameters relative to a suitable threshold, one can identify the presence of one or more target cells in a sample with a higher degree of sensitivity and specificity than that achievable using conventional methods.

Figure 9:
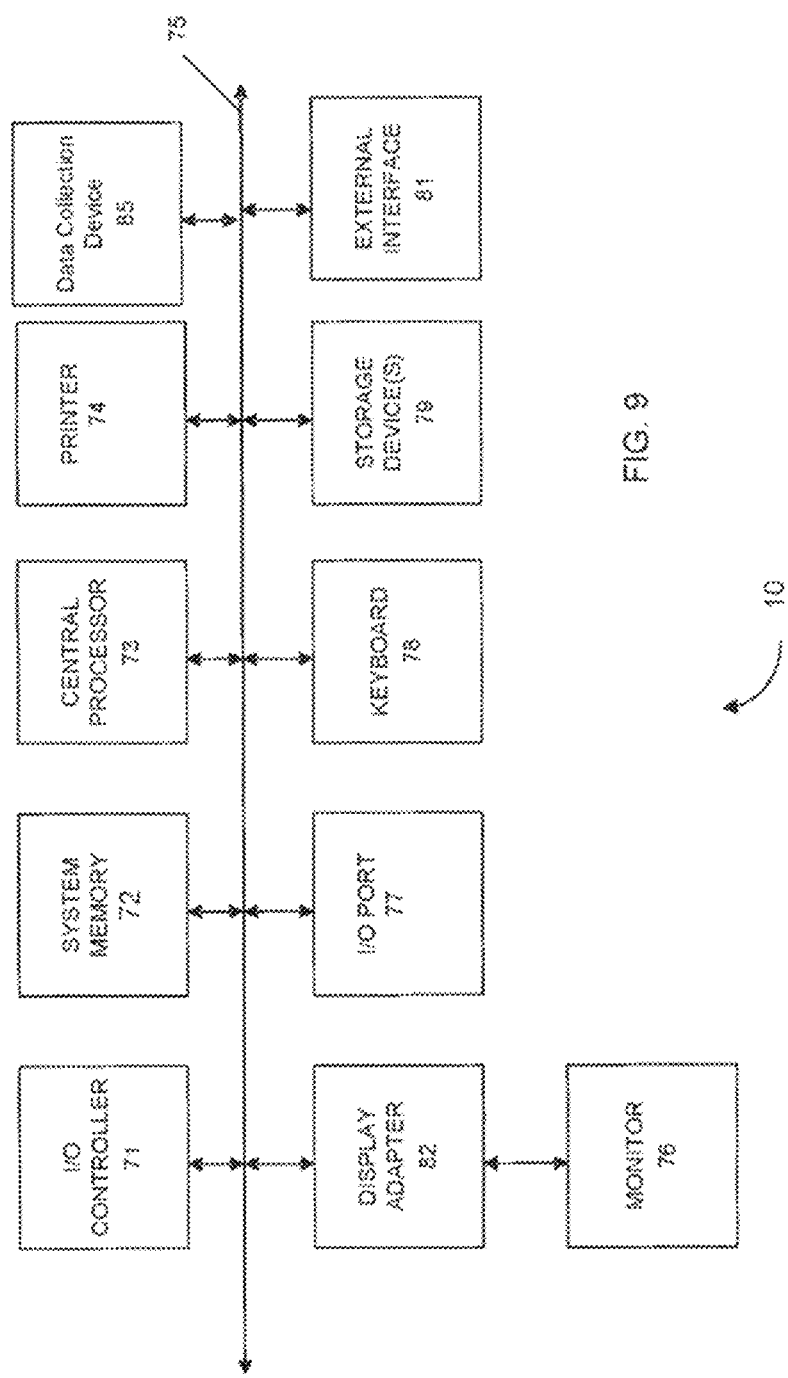
FIG. 9 is a schematic illustration of an exemplary computer system that can be used to perform one or more steps of the method described herein.

The methods described herein can be performed by a system operably connected to a computer system including a processor as described above and illustrated in FIG. 1. A computer system can include desktop and laptop computers, tablets, mobile phones and other mobile devices. As illustrated in FIG. 9, a computer system can include one or more subsystems interconnected via a system bus 75. Additional subsystems such as a printer 74, keyboard 78, storage device(s) 79, monitor 76, which is coupled to display adapter 82, and others are shown. Peripherals and input/output (I/O) devices, which couple to I/O controller 71, can be connected to the computer system by any number of means known in the art such as input/output (I/O) port 77 (e.g., USB, FireWire). For example, I/O port 77 or external interface 81 (e.g. Ethernet, Wi-Fi, etc.) can be used to connect computer system 10 to a wide area network such as the Internet, a mouse input device, or a scanner. The interconnection via system bus 75 allows the central processor 73 to communicate with each subsystem and to control the execution of instructions from system memory 72 or the storage device(s) 79 (e.g., a fixed disk, such as a hard drive, or optical disk), as well as the exchange of information between subsystems. The system memory 72 and/or the storage device(s) 79 may embody a computer readable medium. Another subsystem is a data collection device 85, such as a camera, microphone, accelerometer, and the like. Any of the data mentioned herein can be output from one component to another component and can be output to the user.

A computer system can include a plurality of the same components or subsystems, e.g., connected together by external interface 81 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware (e.g. an application specific integrated circuit or field programmable gate array) and/or using computer software with a generally programmable processor in a modular or integrated manner. As used herein, a processor includes a single-core processor, multi-core processor on a same integrated chip, or multiple processing units on a single circuit board or networked. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, units, circuits, or other means for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the invention has been presented for the purposes of illustration and description. It is not intended to be exhaustive or to limit the invention to the precise form described, and many modifications and variations are possible in light of the teaching above.

EXAMPLES

Example 1. Method of Detecting CRE in a SpectroMax Instrument

A sample including one or more CRE target cells was analyzed in a SpectroMax instrument using the protocol described in U.S. Pat. No. 9,481,903, the disclosure of which is incorporated herein by reference. Briefly, the sample is mixed a plurality of transduction particles in a container and the contents were maintained at a temperature of greater than or equal to room temperature for at least 2 hours. These conditions were sufficient to generate a quantity of reporter molecules to produce a measurable signal. The measurable signal was detected in a SpectraMax® L Microplate Luminometer (Molecular Devices, LLC., Sunnyvale Calif. 94089).

Figure 5:
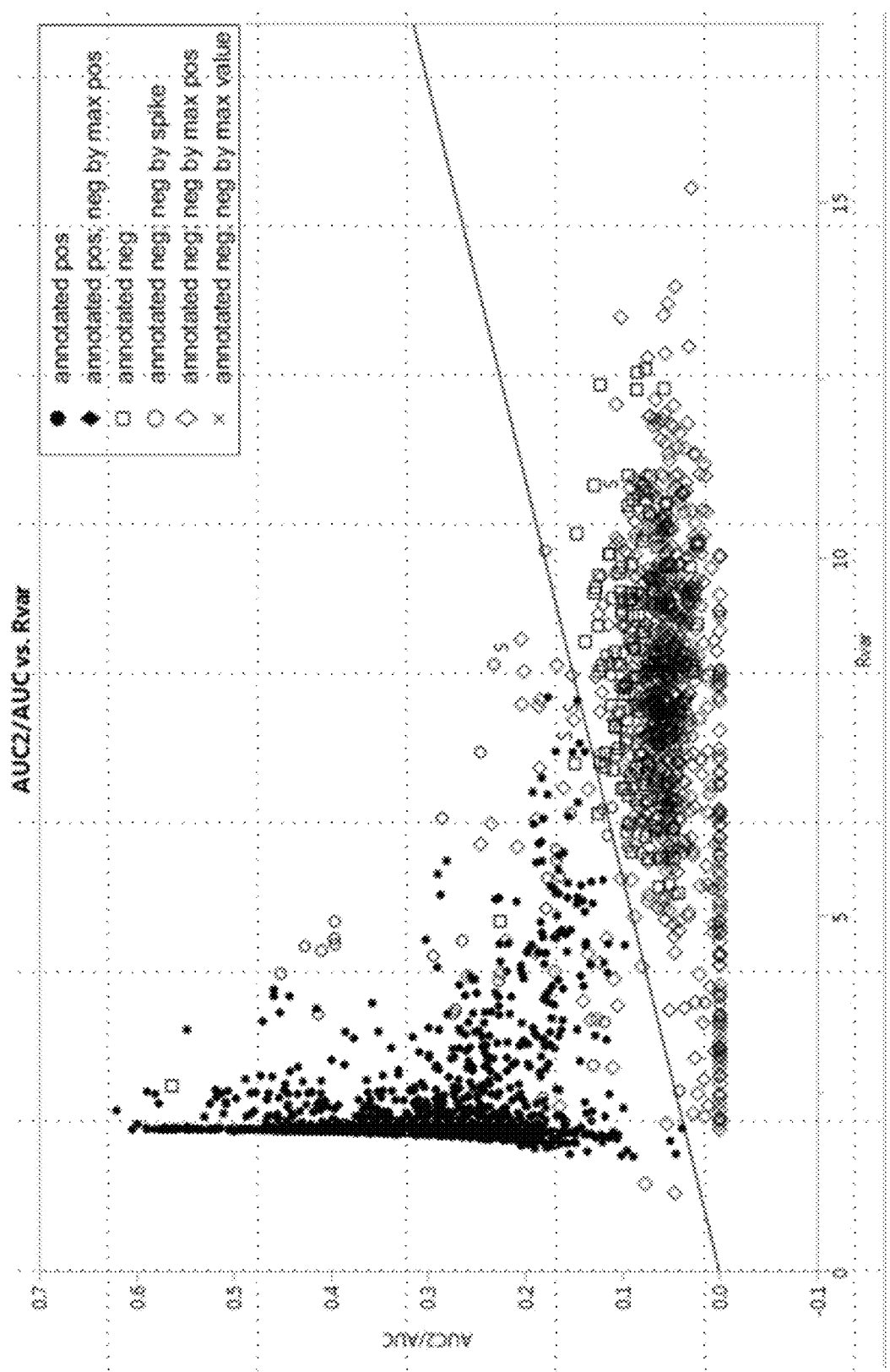
FIG. 5 shows an analysis of the results of an assay performed in a SpectroMax instrument, wherein the figure includes plot of A2/AUC (Area Ratio) versus Rvar for a curve derived from the signal data points detected during the assay.

The curve analysis parameters identified herein were calculated using a processor operably connected to the instrument and FIG. 5 shows a plot of Area Ratio on the y-axis vs. Rvar on the x-axis. Points annotated as positive are shown in solid circle and negative are in open square and the black line (with slope and intercept) partitions the positive and negative signals. As shown in FIG. 5, there are (negative) data in the positive region but these data were called negative by three different criteria: (a) those data points identified using an open circle were called negative due to the presence of spikes; (b) those data points identified using an open diamond were called negative due to the peak being outside the acceptable region; and (c) those data identified by a S were called negative because the eSlope exceeded a threshold.

Figure 6:
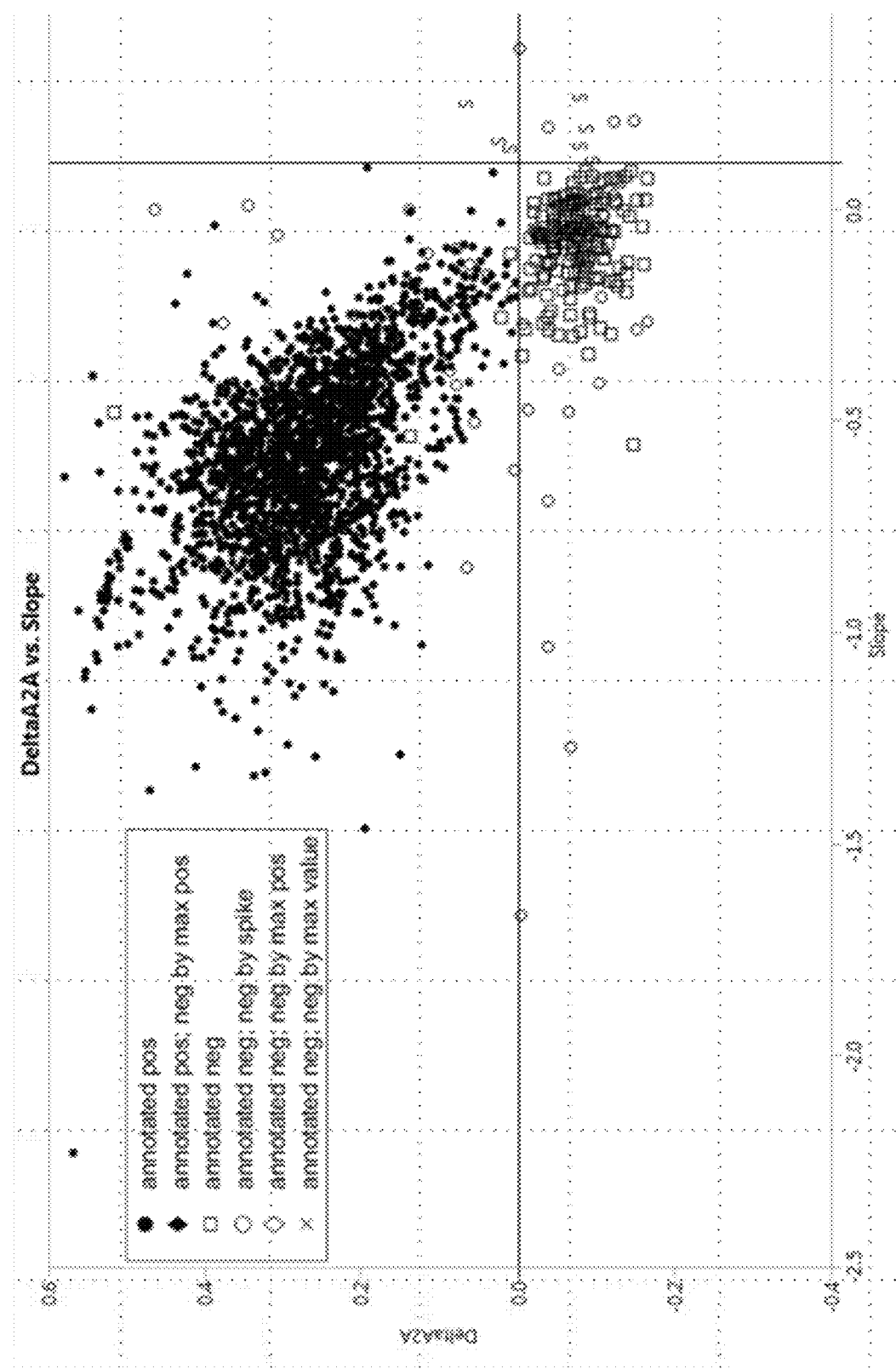
FIG. 6 shows the results of a further analysis of the curve shown in FIG. 5 wherein the distance from the threshold line is plotted vs. eSlope.

FIG. 6 is a plot of distance from the threshold line (y-axis) vs. eSlope (x-axis). In this figure, an eSlope threshold of 0.11 was used, such that points greater than this value were called negative. A comparison of the curve call result vs. the annotated result is shown in Table 1.

TABLE 1

| | Visual call | | | | | | | | |
|---|---|---|---|---|---|---|---|---|---|
| | Positive | | Negative | | Equivocal | | N/A | | |
| Results 1 | N | Column % | N | Column % | N | Column % | N | Column % | N |
| Positive | 2026 | 99.85 | 4 | 0.39 | 17 | 65.38 | 0 | 0.00 | 2047 |
| Negative | 3 | 0.15 | 1021 | 99.61 | 9 | 34.62 | 8 | 100.00 | 1217 |
| All | 2029 | 100.00 | 1025 | 100.00 | 26 | 100.00 | 8 | 100.00 | 3264 |

Example 2. Method of Detecting CRE Using a VivoDx Instrument

Figure 7:
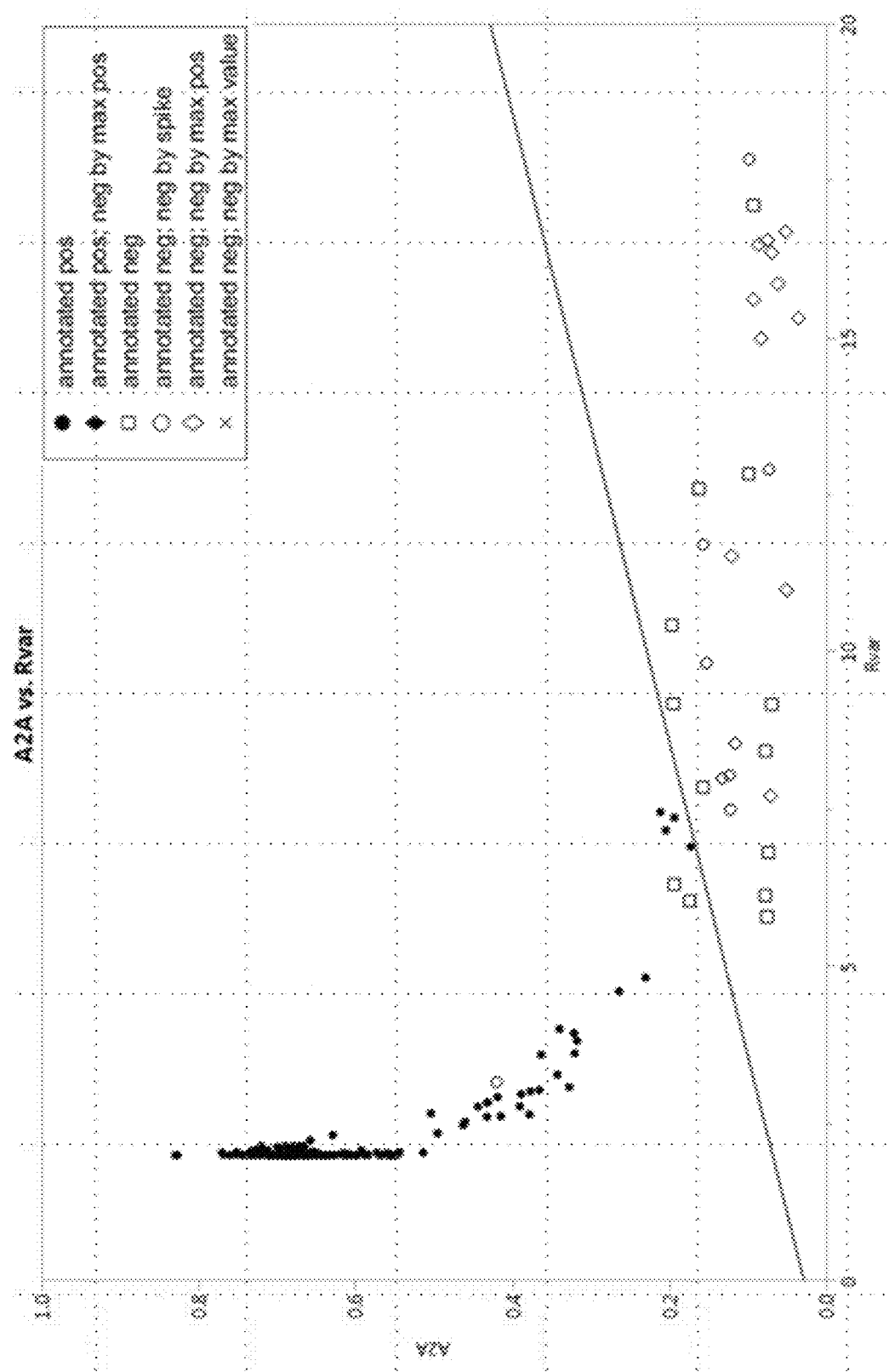
FIG. 7 shows an analysis of the results of an assay performed in a VivoDX instrument, wherein the figure includes a plot of A2/AUC (Area Ratio) versus Rvar for a curve derived from the signal data points detected during the assay.
Figure 8:
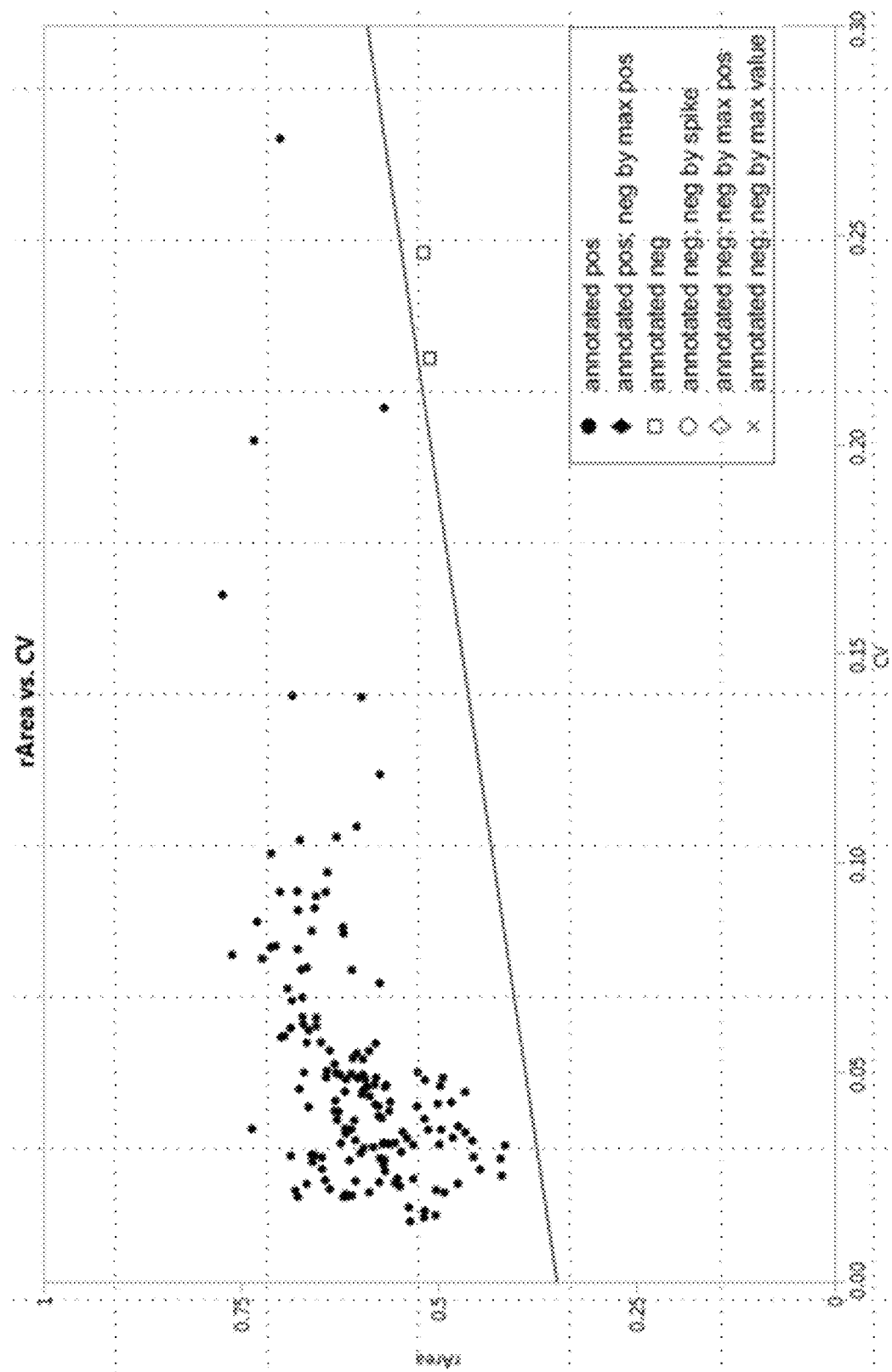
FIG. 8 shows the results of a further analysis of the positive signal data identified from an analysis of FIG. 7, wherein Relative Area is plotted vs. CV.

The sample was prepared and assayed using the method described in Example 1, but the assay was performed in a VivoDx Instrument (Roche Molecular Systems, Inc., Pleasanton, Calif. 94588). FIG. 7 shows the Area Ratio vs. Rvar plot. The data above the threshold line (intermediate positive) were analyzed and the results are shown in FIG. 8, wherein the Relative Area (y-axis) was plotted vs. CV (x-axis). The second portioning of data that are intermediate positive was used to generate a revised positive vs. negative curve call. Table 2 shows the correlation for these data. Using only Area Ratio vs. Rvar (FIG. 7), there were no false negatives and two false positives. However, using the Relative Area vs. CV, there was perfect agreement between annotations and curve call.

TABLE 2

|  | Visual call | | | | |
| --- | --- | --- | --- | --- | --- |
|  | Positive | | Negative | | |
|  | N | Column % | N | Column % | N |
| Results 1 | | | | | |
| Positive | 233 | 100.00 | 2 | 5.5 | 235 |
| Negative | 0 | 0 | 34 | 94.5 | 34 |
| All | 233 | 100.00 | 36 | 100.00 | 269 |
| Results 2 | | | | | |
| Positive | 233 | 100.00 | 0 | 0.00 | 233 |
| Negative | 0 | 0 | 36 | 100.00 | 36 |
| All | 233 | 100.00 | 36 | 100.00 | 269 |

Example 3. Alternative Method of Detecting CRE Using a VivoDx Instrument

The sample was prepared and assayed using the method described in Example 1, but the assay was performed in a VivoDx Instrument using an alternative algorithm. In the method, two different values of the luminescence signal were used: RLU (raw signal) and nRLU (raw signal after passing through a Hampel filter, which was used to detect and remove outliers). All calculations used nRLU except for the following parameters: Rvar (relative variation) and CM (center of mass).

Figure 10:
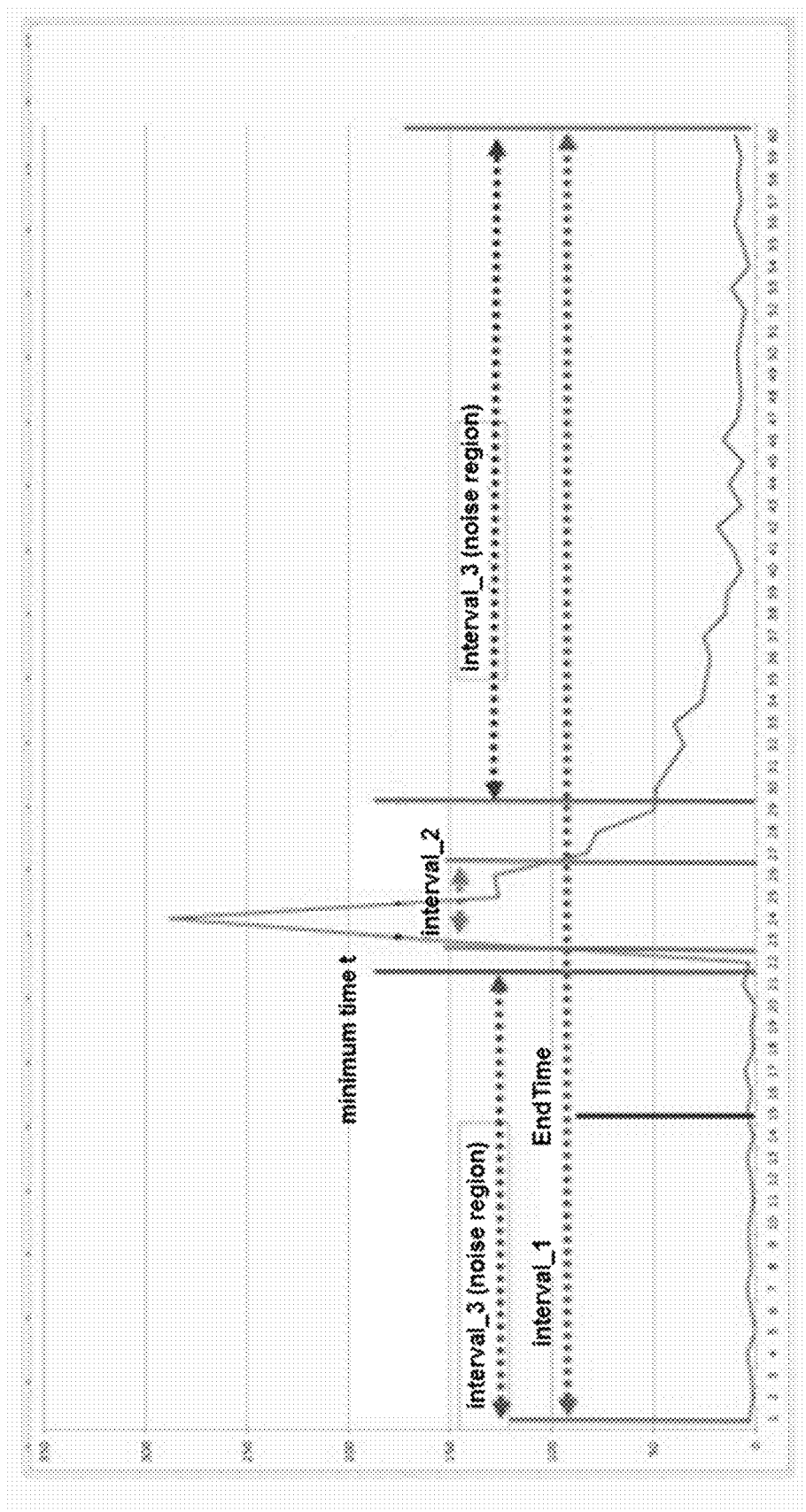
FIG. 10 shows the three time intervals used in internal calculations for the alternative algorithm described below.

As shown in FIG. 10, three time intervals were used in internal calculations of the alternative algorithm. These are labeled as Interval_1, Interval_2, and Interval_3 in FIG. 10. Intervals 2 and 3 are relative and depend on the time associated with the maximum peak. Interval 1 is defined as the set of all times from 0 to EndTime. Interval 2 is defined based on the following conditions: (a) if the maximum of nRLU is between the time interval tMin to tNoise, tPeak is the sequence number of the maximum, i.e., Interval_2= (tPeak−1: tPeak+3); or (b) if the maximum of nRLU is outside the time interval tMin to tNoise, Interval_2=(tMin/ 0.25+1: tMax/0.25+1). Interval 3 is defined based on the following conditions: (a) if the maximum of nRLU is between the time interval tMin to tNoise, tPeak is the sequence number of the maximum and Interval_3=(1: tPeak−2 and tPeak+6: EndTime/0.25+1); or (b) if the maximum of nRLU is outside the time interval tMin to tNoise, Interval_3=(1:tMin/0.25 and tNoise/0.25+2: EndTime/ 0.25+1).

The alternative algorithm was used to determine whether a given luminescence curve was positive or negative, to set spike curves as negative, to set curves with a maximum signal in the wrong interval as negative, to set curves with a center of mass greater than the threshold as invalid, and to determine threshold parameter values by an initial set of annotated data. The following table provides a list of input and output parameters, respectively, for the alternative method:

| Input Parameters | |
| --- | --- |
| Name | Description |
| A2AInt | Intercept of threshold line for A2A vs Rvar |
| A2ASlp | Slope of threshold line for A2A vs Rvar |
| CMMax | Threshold of center of mass |
| EndTime | Last time to use for calculation |
| minRLU | maxRLU (in peak region) threshold value |
| rAreaInt | Intercept of threshold line for rArea vs S2N |
| rAreaSlp | Slope of threshold line for rArea vs S2N |
| Spike | Fractional decrease of RLU required for spike |
| tMin | Start time for integration of area the when relative interval is not used |
| tMax | End time for integration of area the when relative interval is not used |
| tNoise | The last time point in determining the relative peak location |

| Output Parameters | |
| --- | --- |
| Name | Description |
| Area | Total area under RLU curve, Area = $\int_0^{EndTime}$ nRLU dt |
| A2 | Area under peak of RLU curve $$A2 = \int_{Interval\_2} nRLU\, dt$$ |
| A2A | Area ratio: A2/A |
| CM | Center of Mass; CM = sum(RLU(t) × t)/sum(RLU(t)) |
| Curve Call | Final result |
| CV | Coefficient of variation; noise/mSignal |
| Delta_A2A | Data point after subtraction of threshold line of A2A vs Rvar |
| MaxSignal | Maximum signal in peak region (Interval 2) |
| rArea | Relative area: A2/(maximum in interval 2) |
| Rvar | Relative variation |

-continued $$Rvar = \frac{\sum_{i=1}^{n-1} |nRLU_{i+1} - nRLU_i|}{\max(RLU)}, \text{ if } \max(RLU) > 0$$

wherein Rvar = $10^{-6}$, if max(RLU) ≤ 0

| | |
|---|---|
| S2N | Signal to noise ratio; (max signal in the peak region)/noise, using nRLU |
| Result_1 | Curve call using A2A vs Rvar |
| Result_2 | Curve call using rArea vs CV |
| zTest | Validity of curve |
| Noise | calculated in interval 2 as (StandardDeviation (interval 2) using nRLU |
| mSignal | Mean signal is calculated in interval 2 as mean (data(interval 2)), using nRL |

A spike test was used to check whether MaxSignal was a real peak or a spike. A spike is defined as having a luminescence (RLU) value less than or equal to the Baseline one side of MaxSignal, while the first point on the other side as a value less than (spike×MaxSignal) or the second point on the other side of MaxSignal has a value less than (spike/2× MaxSignal). nRLU is used for the spike test; tMS is the time index associated with MaxSignal; baseline is defined as: my=median(nRLU[0 to 5 seconds]), sd=standard deviation (nRLU[0 to 5 seconds]), Baseline=my+3*sd.

Right Spike Test:

RLU(tMS-1)<=Baseline AND {[RLU(tMS+1)
  <spike*MaxSignal] OR [RLU(tMS+2)<spike/
  2*MaxSignal]}.

Left Spike Test:

RLU(tMS+1)<=Baseline AND {[RLU(tMS-1)
  <spike*MaxSignal] OR [RLU(tMS-2)<spike/
  2*MaxSignal]}.

A zTest was used to designate whether the MaxSignal was valid. Possible values of zTest are: zTest=1: if MaxSignal is valid [is the global_maximum, not a spike, between [tMin: tNoise]; zTest=0: if MaxSignal is a spike; zTest=−1 if MaxSignal is outside the range [tMin: tNoise].

Figure 11:
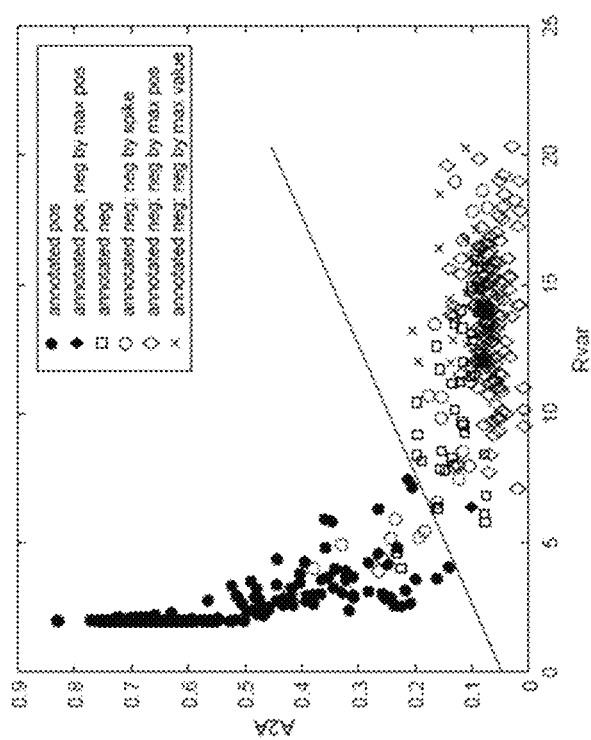
FIG. 11 shows Result_1, which is a Curve Call of either positive or negative using the alternative method, with a plot of A2/A vs. Rvar. The black line through the center of FIG. 11 is a plot of A2AInt+Rvar*A2ASlp and solid points above this line are positive and solid points below this line are negative.

Result_1 is a Curve Call of either positive or negative using the alternative method and it is illustrated in FIG. 11. FIG. 11 shows a plot of A2/A vs. Rvar. Positive points are shown in closed circles, negative points are shown in open squares, open circles represent spikes, open diamonds represent a peak outside the rang tMin to tNoise, X represents curves with a MaxRLU<minRLU, and the black line through the center of FIG. 11 is a plot of A2AInt+ Rvar*A2ASlp. Solid points above this line are positive and solid points below this line are negative.

Figure 12:
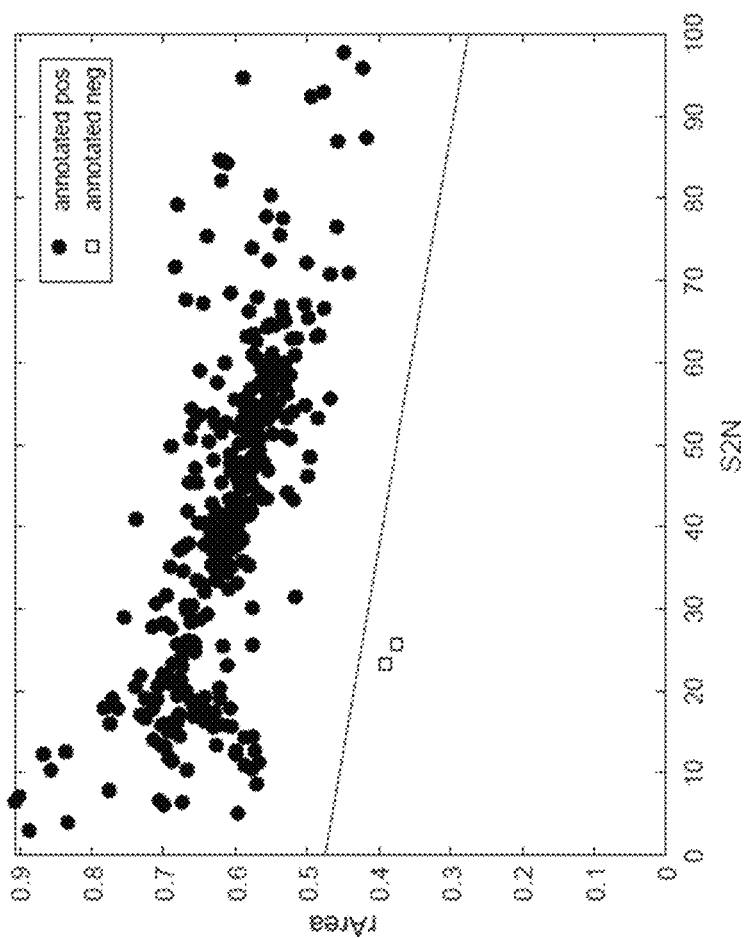
FIG. 12 shows Result_2, which is a Curve Call of either positive or negative using the alternative method. Data points in FIG. 11 with a DeltaA2A>0 are plotted in FIG. 12 and the axes are rArea vs. S2N. The threshold line in FIG. 12 is a plot of rAreaInt+S2N*rAreaSlp, and the data points above the line are positive and those below the line are negative.

Result_2 is a Curve Call of either positive or negative and it is illustrated in FIG. 12. Data points in FIG. 11 with a DeltaA2A>0 are plotted in FIG. 12. The axes in FIG. 12 are rArea vs. S2N. FIG. 12 provided an improvement of the curve call over that using Result_1. The threshold line in FIG. 12 is a plot of rAreaInt+S2N*rAreaSlp, and the data points above the line are positive and those below the line are negative.

Figure 13:
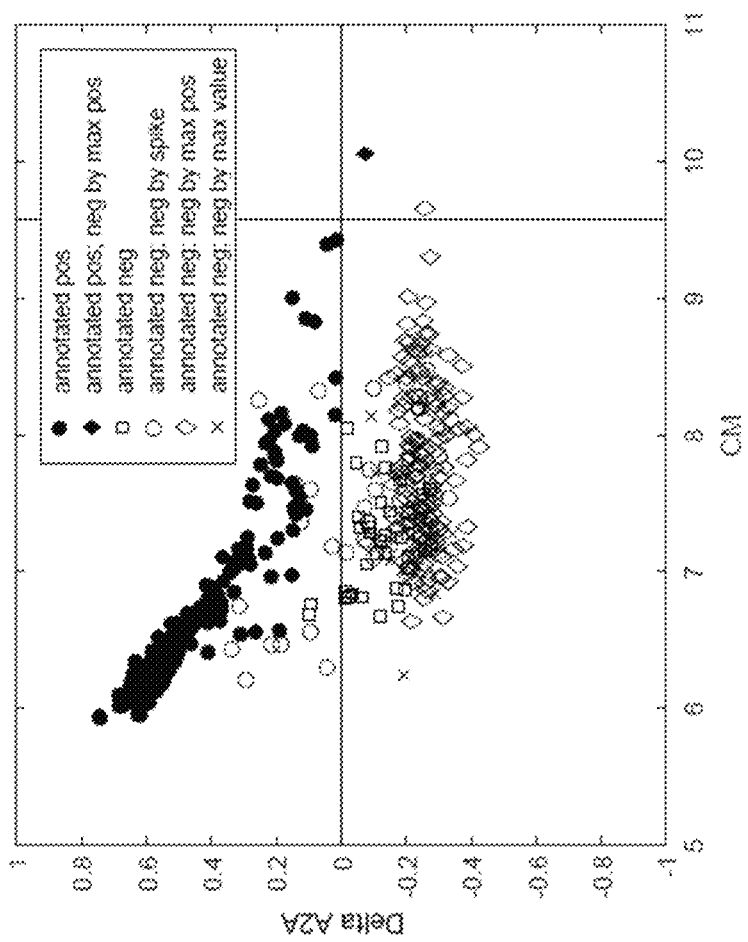
FIG. 13 is a plot of DeltaA2A vs CM, which is used to determine the center of mass (CM) threshold. DeltaA2A is defined as the point on the A2A vs. Rvar plot in FIG. 11 minus the threshold line A2AInt+Rvar*A2ASlp. Curves with a CM>CMMax AND MaxSignal>minRLU and zTest 0 are called invalid.

A plot of DeltaA2A vs CM, as shown in FIG. 13, was used to determine the center of mass (CM) threshold. DeltaA2A is defined as the point on the A2A vs. Rvar plot in FIG. 11 minus the threshold line A2AInt+Rvar*A2ASlp. Curves with a CM>CMMax AND MaxSignal>minRLU and zTest 0 are called invalid.

In the alternative method, the Curve Call was positive if it fell above the line defined by rAreaInt+S2N*rAreaSlp (FIG. 12).

All patents, patent applications, publications, and descriptions mentioned herein are incorporated by reference in their entirety for all purposes. None is admitted to be prior art.

The invention claimed is:

1. A method of detecting one or more target bacterium cells present in a sample, the method comprising the steps of:
   (a) mixing the sample with a plurality of transduction particles capable of binding to the one or more target bacterium cells, wherein the plurality of transduction particles are (i) engineered to include a nucleic acid molecule formulated to cause the one or more target bacterium cells to produce a plurality of reporter molecules capable of generating a detectable luminescence signal, (ii) formulated to bind to and deliver the nucleic acid molecules into the one or more target bacterium cells, and (iii) non-replicative;
   (b) maintaining the sample and the plurality of transduction particles under conditions sufficient to express the plurality of reporter molecules when the one or more target bacterium cells are present in the sample;
   (c) receiving a plurality of signal data points, each associated with a quantity of the plurality of reporter molecules, wherein the plurality of signal data points are indicative of the presence of the one or more target bacterium cells in the sample;
   (d) generating a first curve in which signal intensity of the plurality of signal data points is plotted against time;
   (e) analyzing the first curve by calculating each of the following parameters based on the first curve: Area Under Curve (AUC); Area Under Peak (A2); Area Ratio; Global Maximum Intensity (globalmaxRLU); and Relative Variation (Rvar); and
   (f) detecting the one or more target bacterium cells present in the sample by comparing Area Ratio and Rvar and applying a linear threshold to identify a set of positive signal data points, wherein said set of positive signal data points reflect the presence of the one or more target bacterium cells in the sample,
   wherein Area Ratio=A2/AUC and wherein the linear threshold is A2AInt+Rvar*A2ASlp,
   wherein A2AInt is an intercept of a threshold line for A2A vs. Rvar; Rvar is $$Rvar = \frac{\sum_{i=1}^{n-1} |nRLU_{i+1} - nRLU_i|}{\max(RLU)}, \text{ if } \max(RLU) > 0$$

and A2ASlp is a slope of the threshold line for A2A vs. Rvar.

2. The method of claim 1, further comprising: analyzing the first curve by further calculating at least one of the following parameters based on the first curve: Signal to Noise Ratio (S2N); Coefficient of Variation (CV); Spike Detection; Peak Position; Exponential Slope (eSlope); Center of Mass (CM); and Relative Area (rArea).

3. The method of claim 1 wherein rArea=A2/(maximum signal in a peak region).

4. The method of claim 2 further comprising calculating rAreaInt+S2N*rAreaSlp.

5. The method of claim 1 wherein AUC is calculated using a trapezoidal method.

6. The method of claim 1 wherein A2 is defined over a fixed time interval.

7. The method of claim 1 wherein A2 is defined over a variable time interval.

8. The method of claim 6 wherein the fixed time interval ranges from −0.10 seconds to +10.0 seconds relative to a selected peak time in the first curve.

9. The method of claim 7 wherein the variable time interval is variable between −0.25 seconds <selected peak time in the first curve in seconds <+2.00 seconds.

* * * * *